(12) United States Patent
Rheinheimer et al.

(10) Patent No.: US 6,500,950 B1
(45) Date of Patent: Dec. 31, 2002

(54) BENZYLIDENEPYRAZOLONES, THEIR PREPARATION AND USE

(75) Inventors: Joachim Rheinheimer, Ludwigshafen (DE); Matthias Witschel, Ludwigshafen (DE); Stefan Engel, Wörrstadt (DE); Ernst Baumann, Dudenhofen (DE); Wolfgang von Deyn, Neustadt (DE); Regina Luise Hill, Harthausen (DE); Guido Mayer, Neustadt (DE); Ulf Misslitz, Neustadt (DE); Oliver Wagner, Ludwigshafen (DE); Martina Otten, Ludwigshafen (DE); Karl-Otto Westphalen, Speyer (DE); Helmut Walter, Obrigheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 5 days.

(21) Appl. No.: 09/765,626

(22) Filed: Jan. 22, 2001

Related U.S. Application Data

(62) Division of application No. 09/554,184, filed as application No. PCT/EP98/07099 on Jun. 11, 1998, now Pat. No. 6,271,179.

(30) Foreign Application Priority Data

Nov. 21, 1997 (DE) .......................... 197 51 722

(51) Int. Cl.$^7$ ............................................ C07D 413/10
(52) U.S. Cl. .................. 544/140; 544/238; 544/335; 546/211; 546/275.4; 548/128; 548/131; 548/143; 548/204; 548/235; 548/266.5; 548/376.1
(58) Field of Search ................. 544/140, 238, 544/335; 546/211, 275.4; 548/128, 131, 143, 204, 235, 266.5, 376.1

(56) References Cited

U.S. PATENT DOCUMENTS 4,063,925 A * 12/1977 Konotsune et al. ......... 548/367
4,885,022 A * 12/1989 Baba et al. ................. 548/103

* cited by examiner

Primary Examiner—Joseph K. McKane
Assistant Examiner—Kamal Saeed
(74) Attorney, Agent, or Firm—Keil & Weinkauf

(57) ABSTRACT

Benzylidenepyrazolones of the formula I,

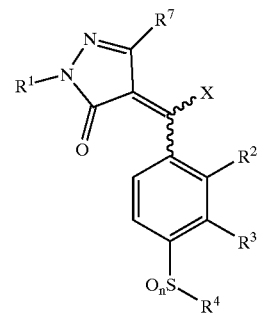

where the substituents and the index n have the following meanings:

$R^1$ is unsubstituted or substituted $C_1-C_6$-alkyl;

$R^2$ is unsubstituted or substituted $C_1-C_6$-alkyl, unsubstituted or substituted $C_1-C_6$-alkoxy, halogen, nitro, cyano;

$R^3$ is hydrogen, halogen, nitro, cyano, a group $NR^5R^6$, $OCOR^5$, $NR^5COR^6$, $CO_2R^5$, —$COSR^5$, —$CONR^5R^6$, $C_1-C_4$-alkoxyiminoalkyl, $C_1-C_6$-alkylcarbonyl, unsubstituted or substituted $C_1-C_6$-alkyl, unsubstituted or substituted $C_1-C_6$-alkoxy, unsubstituted or substituted $C_1-C_6$-alkylthio, unsubstituted or substituted $C_2-C_6$-alkenyl, unsubstituted or substituted $C_2-C_6$-alkynyl, unsubstituted or substituted phenyl, unsubstituted or substituted phenoxy, an unsubstituted or substituted 5- or 6-membered saturated or unsaturated heterocycle which may contain up to 4 nitrogen atoms and/or up to 2 oxygen or sulfur atoms as ring members;

$R^4$ is $C_1-C_6$-alkyl, $C_1-C_4$-haloalkyl;

$R^3$ and $R^4$ form an optionally substituted saturated or unsaturated 2- or 3-membered bridge which may contain a sulfur atom which may be oxidized to the sulfoxide or sulfone;

$R^5$ is hydrogen or unsubstituted or substituted $C_1-C_6$-alkyl;

$R^6$ is unsubstituted or substituted $C_1-C_6$-alkyl;

$R^7$ is hydrogen, $C_1-C_6$-alkyl or $C_1-C_4$-haloalkyl;

n is 0,1 or 2,

X is hydrogen, chlorine or bromine;

where the compounds claimed may be present both in the trans and in the cis form or as a mixture of these isomers, are described.

15 Claims, No Drawings

BENZYLIDENEPYRAZOLONES, THEIR PREPARATION AND USE

This is a Divisional application of application Ser. No. 09/554,184, filed May 11, 2000, PCT/EP98/07099 filed Jun. 11, 1998 now U.S. Pat. No. 6,271,179 (allowed), under 35 U.S.C. 0371.

The present invention relates to benzylidenepyrazolones of the formula I

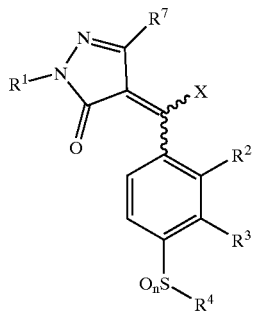

where the substituents and the index n have the following meanings:

$R^1$ is unsubstituted or substituted $C_1$–$C_6$-alkyl;

$R^2$ is unsubstituted or substituted $C_1$–$C_6$-alkyl, unsubstituted or substituted $C_1$–$C_6$-alkoxy, halogen, nitro, cyano;

$R^3$ is hydrogen, halogen, nitro, cyano, a group $NR^5R^6$, $OCOR^5$, $NR^5COR^6$, $CO_2R^5$, —$COSR^5$, —$CONR^5R^6$, $C_1$–$C_4$-alkoxyiminoalkyl, $C_1$–$C_6$-alkylcarbonyl, unsubstituted or substituted $C_1$–$C_6$-alkyl, unsubstituted or substituted $C_1$–$C_6$-alkoxy, unsubstituted or substituted $C_1$–$C_6$-alkylthio, unsubstituted or substituted $C_2$–$C_6$-alkenyl, unsubstituted or substituted $C_2$–$C_6$-alkynyl, unsubstituted or substituted phenyl, unsubstituted or substituted phenoxy, an unsubstituted or substituted 5- or 6-membered saturated or unsaturated heterocycle which may contain up to 4 nitrogen atoms and/or up to 2 oxygen or sulfur atoms as ring members;

$R^4$ is $C_1$–$C_6$-alkyl, $C_1$–$C_4$-haloalkyl; or $R^3$ and $R^4$ form an optionally substituted saturated or unsaturated 2- or 3-membered bridge which may contain a sulfur atom which may be oxidized to give sulfoxide or sulfone;

$R^5$ is hydrogen or unsubstituted or substituted $C_1$–$C_6$-alkyl;

$R^6$ is unsubstituted or substituted $C_1$–$C_6$-alkyl;

$R^7$ is hydrogen, $C_1$–$C_6$-alkyl or $C_1$–$C_4$-haloalkyl;

n is 0, 1 or 2;

x is hydrogen, chlorine or bromine;

where the compounds claimed may be present both in the trans and in the cis form or as a mixture of these isomers.

Furthermore, the present invention relates to compositions which comprise the compounds of the formula I, and to the use of the compounds I and of compositions comprising them for controlling harmful plants, to novel benzoylpyrazoles of the formula II and to a process for preparing the compounds I and II.

Herbicidally active 4-benzoylpyrazoles are disclosed in the literature, for example in EP-A 282 944 or WO 96/26206. However, 4-benzoyl-5-chloropyrazoles have hitherto not been described. In EP-A 282 944, it is only mentioned in a general way that the reaction of 4-benzoyl-5-hydroxypyrazoles with acyl halides should lead to 4-benzoyl-5-chloropyrazoles.

Benzylidenepyrazolones, some of which have herbicidal activity, are disclosed in U.S. Pat. No. 4,382,948 and JP 61268670. All the structures of the prior art have a very specific substitution pattern in the phenyl moiety of the benzylidenepyrazolone: in the position para to the methyne bridge, for example, there is in each case a hydrogen or halogen atom or a trifluoromethyl or nitro group.

However, the herbicidal properties of the prior art compounds and their compatibility with crop plants are not entirely satisfactory.

It is an object of the present invention to provide novel, in particular herbicidally active, compounds having improved properties.

We have found that this object is achieved by the benzylidenepyrazolones of the formula I according to the invention and by their herbicidal activity.

The present invention also provides stereoisomers of the compounds of the formula I. Both pure stereoisomers and mixtures thereof are included.

The compounds of the formula I may be present as cis or trans isomers and may contain, depending on the substitution pattern, one or more chiral centers, in which case they may also be present as mixtures of enantiomers or diastereomers. The invention provides both the pure isomers, enantiomers or diastereomers and mixtures thereof.

Benzylidenepyrazolones of the formula I and benzoylpyrazoles of the formula II according to the invention can be prepared as described below.

Benzylidenepyrazolones of the formula Ia (X=hydrogen) can be synthesized by Knoevenagel condensation of pyrazolones of the formula III, in which the radicals $R^1$ and $R^7$ are as defined above, and a substituted benzaldehyde of the formula IV, in which the radicals $R^2$ to $R^4$ are as defined above, similarly to the method described in U.S. Pat. No. 4,382,948.

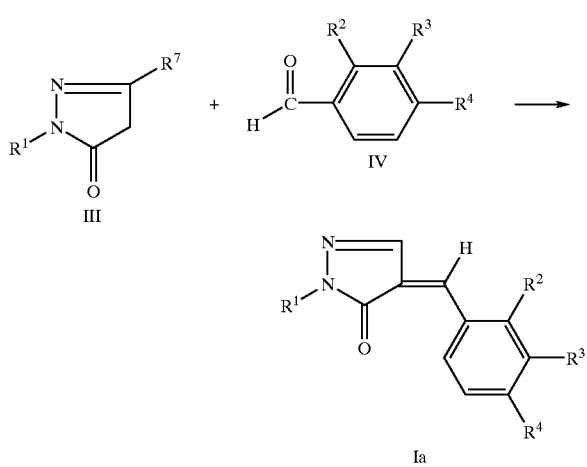

Furthermore, the compounds Ia are obtainable for example by reductive dehalogenation from compounds of the formula I in which X is bromine.

Benzylidenepyrazolones Ib (X=bromine or chlorine) can be prepared from the compounds Ia described above by halogenation with bromine or chlorine and subsequent dehydrohalogenation in the presence of base.

The benzylidenepyrazolones Ib are preferably obtained from ketones of the formula V, which are either known or which can be prepared similarly to known compounds (see DE-A 19709118.0 and WO 96/26200), by reaction with acyl halides.

Suitable acyl halides are, for example, the halides of sulfuric acid, carbonic acid and phosphoric acid. For the exchange with chlorine, preference is given to using thionyl chloride, phosgene, phosphorus pentachloride and particularly preferably phosphorus oxychloride. For the exchange with bromine, preference is given to using phosphorus oxybromide.

The reaction can be carried out in a customary manner, with or without solvent or with a solvent which is inert under the reaction conditions. Generally, it is possible to control the selectivity of the reaction by addition of a base of low nucleophilicity such as, for example, pyridine, dimethylaminopyridine or dimethylformamide.

The reaction temperature is generally from 0° C. to 200° C., preferably from 50° C. to 140° C.

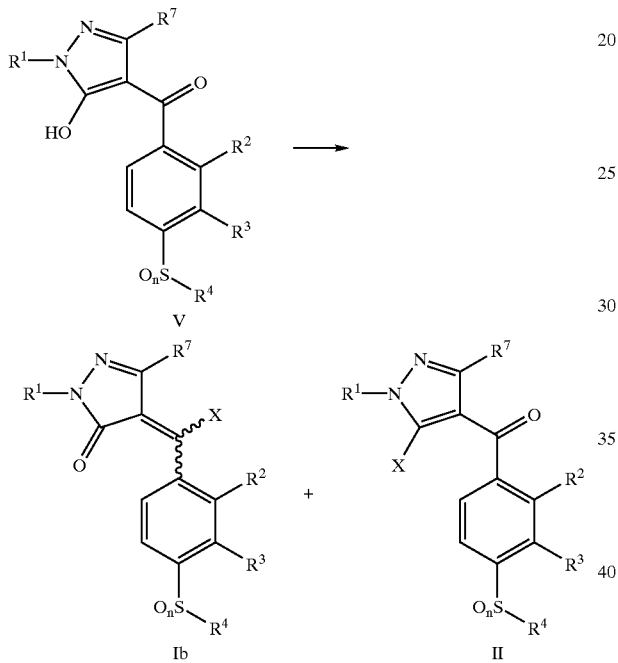

In this reaction, a mixture of both isomers with respect to the newly formed double bond may be obtained. In this case, the isomers can be separated, if required (for example by crystallization, extraction or chromatography).

A byproduct of this reaction are the compounds II which, depending on the substitution pattern and the way in which the reaction is carried out, may be obtained in smaller, similar or higher proportions. Many of these compounds are novel, and they are of considerable interest as precursors for herbicidally active compounds (see for example EP-A 282 944).

The organic moieties mentioned for the substituents $R^1$–$R^7$ or as radicals on phenyl rings or heterocycles represent collective terms for lists of the individual group members. All hydrocarbon chains, ie. all alkyl, haloalkyl, cycloalkyl, alkoxy, haloalkoxy, alkylcarbonyl, alkenyl, alkynyl moieties may be straight-chain or branched. Unless stated otherwise, halogenated substituents preferably carry one to five identical or different halogen atoms. Halogen is in each case fluorine, chlorine, bromine or iodine.

Examples of other meanings are:
$C_1$–$C_4$-alkyl and the alkyl moieties of other radicals such as, for example, $C_1$–$C_4$-alkoxy, $C_1$–$C_4$-alkylcarbonyl, $C_1$–$C_4$-alkylthio: methyl, ethyl, n-propyl, 1-methylethyl, butyl, 1-methylpropyl, 2-methylpropyl and 1,1-dimethylethyl;

$C_1$–$C_6$-alkyl and the alkyl moieties of other radicals such as, for example, $C_1$–$C_6$-alkoxy, $C_1$–$C_6$-alkylcarbonyl, $C_1$–$C_6$-alkylthio: $C_1$–$C_4$-alkyl as mentioned above, and pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1-ethyl-1-methylpropyl and 1-ethyl-3-methylpropyl;

$C_1$–$C_4$-haloalkyl: a $C_1$–$C_4$-alkyl radical as mentioned above which is partially or fully substituted by fluorine, chlorine, bromine and/or iodine, ie. for example chloromethyl, dichloromethyl, trichloromethyl, fluoromethyl, difluoromethyl, trifluoromethyl, chlorofluoromethyl, dichlorofluoromethyl, chlorodifluoromethyl, 2-fluoroethyl, 2-chloroethyl, 2-bromoethyl, 2-iodoethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl, 2-fluoropropyl, 3-fluoropropyl, 2,2-difluoropropyl, 2,3-difluoropropyl, 2-chloropropyl, 3-chloropropyl, 2,3-dichloropropyl, 2-bromopropyl, 3-bromopropyl, 3,3,3-trifluoropropyl, 3,3,3-trichloropropyl, 2,2,3,3,3-pentafluoropropyl, heptafluoropropyl, 1-(fluoromethyl)-2-fluoroethyl, 1-(chloromethyl)-2-chloroethyl, 1-(bromomethyl)-2-bromoethyl, 4-fluorobutyl, 4-chlorobutyl, 4-bromobutyl and nonafluorobutyl;

$C_1$–$C_4$-haloalkoxy: a $C_1$–$C_4$-alkoxy radical as mentioned above which is partially or fully substituted by fluorine, chlorine, bromine and/or iodine, ie. for example fluoromethoxy, difluoromethoxy, trifluoromethoxy, chlorodifluoromethoxy, bromodifluoromethoxy, 2-fluoroethoxy, 2-chloroethoxy, 2-bromoethoxy, 2-iodoethoxy, 2,2-difluoroethoxy, 2,2,2-trifluoroethoxy, 2-chloro-2-fluoroethoxy, 2-chloro-2,2-difluoroethoxy, 2,2-dichloro-2-fluoroethoxy, 2,2,2-trichloroethoxy, pentafluoroethoxy, 2-fluoropropoxy, 3-fluoropropoxy, 2-chloropropoxy, 3-chloropropoxy, 2-bromopropoxy, 3-bromopropoxy, 2,2-difluoropropoxy, 2,3-difluoropropoxy, 2,3-dichloropropoxy, 3,3,3-trifluoropropoxy, 3,3,3-trichloropropoxy, 2,2,3,3,3-pentafluoropropoxy, heptafluoropropoxy, 1-(fluoromethyl)-2-fluoroethoxy, 1-(chloromethyl)-2-chloroethoxy, 1-(bromomethyl)-2-bromoethoxy, 4-fluorobutoxy, 4-chlorobutoxy, 4-bromobutoxy and nonafluorobutoxy;

$C_2$–$C_6$-alkenyl: ethenyl, prop-1-en-1-yl, prop-2-en-1-yl, 1-methylethenyl, buten-1-yl, buten-2-yl, buten-3-yl, 1-methyl-prop-1-en-1-yl, 2-methylprop-1-en-1-yl, 1-methylprop-2-en-1-yl, 2-methylprop-2-en-1-yl, penten-1-yl, penten-2-yl, penten-3-yl, penten-4-yl, 1-methylbut-1-en-1-yl, 2-methylbut-1-en-1-yl, 3-methylbut-1-en-1-yl, 1-methylbut-2-en-1-yl, 2-methyl-but-2-en-1-yl, 3-methylbut-2-en-1-yl, 1-methylbut-3-en-1-yl, 2-methylbut-3-en-1-yl, 3-methylbut-3-en-1-yl, 1,1-dimethyl-prop-2-en-1-yl, 1,2-dimethylprop-1-en-1-yl, 1,2-dimethyl-prop-2-en-1-yl, 1-ethylprop-1-en-2-yl, 1-ethylprop-2-en-1-yl, hex-1-en-1-yl, hex-2-en-1-yl, hex-3-en-1-yl, hex-4-en-1-yl, hex-5-en-1-yl, 1-methylpent-1-en-1-yl, 2-methylpent-1-en-1-yl, 3-methylpent-1-en-1-yl, 4-methylpent-1-en-1-yl, 1-methyl-pent-2-en-1-yl, 2-methylpent-2-en-1-yl, 3-methylpent-2-en-1-yl, 4-methylpent-2-en-1-yl, 1-methylpent-3-en-1-yl, 2-methyl-pent-3-en-1-yl, 3-methylpent-3-en-1-yl, 4-methylpent-3-en-1-yl, 1-methylpent-4-en-1-yl, 2-methylpent-4-en-1-yl, 3-methyl-pent-4-en-1-yl, 4-methylpent-4-en-1-yl, 1,1-dimethylbut-2-en-1-yl, 1,1-dimethylbut-3-en-1-yl, 1,2-dimethylbut-1-en-1-yl, 1,2-dimethylbut-2-en-1-yl, 1,2-dimethylbut-3-en-1-yl, 1,3-dimethylbut-1-en-1-yl, 1,3-dimethylbut-2-en-1-yl, 1,3-dimethylbut-3-en-1-yl, 2,2-dimethylbut-3-en-1-yl, 2,3-dimethylbut-1-en-1-yl, 2,3-dimethylbut-2-en-1-yl, 2,3-dimethylbut-3-en-1-yl, 3,3-dimethylbut-1-en-1-yl, 3,3-dimethylbut-2-en-1-yl, 1-ethylbut-1-en-1-yl, 1-ethylbut-2-en-1-yl, 1-ethylbut-3-en-1-yl, 2-ethylbut-1-en-1-yl, 2-ethyl-but-2-en-1-yl, 2-ethylbut-3-en-1-yl, 1,1,2-trimethylprop-2-en-1-yl, 1-ethyl-1-methylprop-2-en-1-yl, 1-ethyl-2-methyl-prop-1-en-1-yl and 1-ethyl-2-methylprop-2-en-1-yl;

$C_2$–$C_6$-alkynyl: ethynyl, prop-1-yn-1-yl, prop-2-yn-1-yl, but-1-yn-1-yl, but-1-yn-3-yl, but-1-yn-4-yl, but-2-yn-1-yl, pent-1-yn-1-yl, pent-1-yn-3-yl, pent-1-yn-4-yl, pent-1-yn-5-yl, pent-2-yn-1-yl, pent-2-yn-4-yl, pent-2-yn-5-yl, 3-methylbut-1-yn-3-yl, 3-methylbut-1-yn-4-yl, hex-1-yn-1-yl, hex-1-yn-3-yl, hex-1-yn-4-yl, hex-1-yn-5-yl, hex-1-yn-6-yl, hex-2-yn-1-yl, hex-2-yn-4-yl, hex-2-yn-5-yl, hex-2-yn-6-yl, hex-3-yn-1-yl, hex-3-yn-2-yl, 3-methylpent-1-yn-1-yl, 3-methylpent-1-yn-3-yl, 3-methylpent-1-yn-4-yl, 3-methylpent-1-yn-5-yl, 4-methylpent-1-yn-1-yl, 4-methylpent-2-yn-4-yl and 4-methyl-pent-2-yn-5-yl;

$C_3$-$C_6$-cycloalkyl: cyclopropyl, cyclobutyl, cyclopentyl and cyclohexyl;

an unsubstituted or substituted 5- or 6-membered saturated or unsaturated heterocycle which may contain up to 4 nitrogen atoms and/or up to 2 oxygen or sulfur atoms as ring members, such as 2-tetrahydrofuranyl, 3-tetrahydrofuranyl, 2-tetrahydrothienyl, 3-tetrahydrothienyl, 2-pyrrolidinyl, 3-pyrrolidinyl, 3-isoxazolidinyl, 4-isoxazolidinyl, 5-isoxazolidinyl, 3-isothiazolidinyl, 4-isothiazolidinyl, 5-isothiazolidinyl, 3-pyrazolidinyl, 4-pyrazolidinyl, 5-pyrazolidinyl, 2-oxazolidinyl, 4-oxazolidinyl, 5-oxazolidinyl, 2-thiazolidinyl, 4-thiazolidinyl, 5-thiazolidinyl, 2-imidazolidinyl, 4-imidazolidinyl, 1,2,4-oxadiazolidin-3-yl, 1,2,4-oxadiazolidin-5-yl, 1,2,4-thiadiazolidin-3-yl, 1,2,4-thiadiazolidin-5-yl, 1,2,4-triazolidin-3-yl, 1,3,4-oxadiazolidin-2-yl, 1,3,4-thiadiazolidin-2-yl, 1,3,4-triazolidin-2-yl, 2,3-dihydrofuran-2-yl, 2,3-dihydrofuran-3-yl, 2,3-dihydrofuran-4-yl, 2,3-dihydrofuran-5-yl, 2,5-dihydrofuran-2-yl, 2,5-dihydrofuran-3-yl, 2,3-dihydrothien-2-yl, 2,3-dihydrothien-3-yl, 2,3-dihydrothien-4-yl, 2,3-dihydrothien-5-yl, 2,5-dihydrothien-2-yl, 2,5-dihydrothien-3-yl, 2,3-dihydropyrrol-2-yl, 2,3-dihydropyrrol-3-yl, 2,3-dihydropyrrol-4-yl, 2,3-dihydropyrrol-5-yl, 2,5-dihydropyrrol-2-yl, 2,5-dihydropyrrol-3-yl, 2,3-dihydroisoxazol-3-yl, 2,3-dihydroisoxazol-4-yl, 2,3-dihydroisoxazol-5-yl, 4,5-dihydroisoxazol-3-yl, 4,5-dihydroisoxazol-4-yl, 4,5-dihydroisoxazol-5-yl, 2,5-dihydroisoxazol-3-yl, 2,5-dihydroisoxazol-4-yl, 2,5-dihydroxazol-5-yl, 2,3-dihydroisothiazol-3-yl, 2,3-dihydroisothiazol-4-yl, 2,3-dihydroisothiazol-5-yl, 4,5-dihydroisothiazol-3-yl, 4,5-dihydroisothiazol-4-yl, 4,5-dihydroisothiazol-5-yl, 2,5-dihydroisothiazol-3-yl, 2,5-dihydroisothiazol-4-yl, 2,5-dihydroisothiazol-5-yl, 2,3-dihydropyrazol-3-yl, 2,3-dihydropyrazol-4-yl, 2,3-dihydropyrazol-5-yl, 4,5-dihydropyrazol-3-yl, 4,5-dihydropyrazol-4-yl, 4,5-dihydropyrazol-5-yl, 2,5-dihydropyrazol-3-yl, 2,5-dihydropyrazol-4-yl, 2,5-dihydropyrazol-5-yl, 2,3-dihydrooxazol-2-yl, 2,3-dihydrooxazol-4-yl, 2,3-dihydrooxazol-5-yl, 4,5-dihydrooxazol-2-yl, 4,5-dihydrooxazol-4-yl, 4,5-dihydrooxazol-5-yl, 2,5-dihydrooxazol-2-yl, 2,5-dihydrooxazol-4-yl, 2,5-dihydrooxazol-5-yl, 2,3-dihydrothiazol-2-yl, 2,3-dihydrothiazol-4-yl, 2,3-dihydrothiazol-5-yl, 4,5-dihydrothiazol-2-yl, 4,5-dihydrothiazol-4-yl, 4,5-dihydrothiazol-5-yl, 2,5-dihydrothiazol-2-yl, 2,5-dihydrothiazol-4-yl, 2,5-dihydrothiazol-5-yl, 2,3-dihydroimidazol-2-yl, 2,3-dihydroimidazol-4-yl, 2,3-dihydroimidazol-5-yl, 4,5-dihydroimidazol-2-yl, 4,5-dihydroimidazol-4-yl, 4,5-dihydroimidazol-5-yl, 2,5-dihydroimidazol-2-yl, 2,5-dihydroimidazol-4-yl, 2,5-dihydroimidazol-5-yl, 2-morpholinyl, 3-morpholinyl, 2-piperidinyl, 3-piperidinyl, 4-piperidinyl, 3-tetrahydropyridazinyl, 4-tetrahydropyridazinyl, 2-tetrahydropyrimidinyl, 4-tetrahydropyrimidinyl, 5-tetrahydropyrimidinyl, 2-tetrahydropyrazinyl, 1,3,5-tetrahydrotriazin-2-yl, 1,2,4-tetrahydrotriazin-3-yl, 1,3-dihydrooxazin-2-yl, 1,3-dithian-2-yl, 2-tetrahydropyranyl, 3-tetrahydropyranyl, 4-tetrahydropyranyl, 2-tetrahydrothiopyranyl, 3-tetrahydrothiopyranyl, 4-tetrahydrothiopyranyl, 1,3-dioxolan-2-yl, 3,4,5,6-tetrahydropyridin-2-yl, 4H-1,3-thiazin-2-yl, 4H-, 1,1-dioxo-2,3,4,5-tetrahydrothien-2-yl, 1,3-dihydrooxazin-2-yl, 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, tetrazol-5-yl, tetrazol-1-yl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl, 1,3,4-triazol-2-yl, 2-pyridinyl, 3-pyridinyl, 4-pyridinyl, 3-pyridazinyl, 4-pyridazinyl, 2-pyrimidinyl, 4-pyrimidinyl, 5-pyrimidinyl, 2-pyrazinyl, 1,3,5-triazin-2-yl, 1,2,4-triazin-3-yl, 1,2,4,5-tetrazin-3-yl.

With respect to the herbicidal activity of the benzylidenepyrazoles I, particular preference is given to the following meanings of the substituents, in each case either alone or in combination:

$R^1$ is $C_1$–$C_4$-alkyl or $C_1$–$C_4$-haloalkyl;

$R^2$ is $C_1$–$C_4$-alkyl, $C_1$–$C_4$-haloalkyl, $C_1$–$C_4$-alkoxy, $C_1$–$C_4$-haloalkoxy, halogen, nitro, cyano;

$R^3$ is hydrogen, halogen, nitro, cyano, a group $NR^5R^6$, $OCOR^5$, $NR^5COR^6$, $CO_2R^5$, —$COSR^5$, —$CONR^5R^6$, $C_1$–$C_4$-alkoxyiminoalkyl, $C_1$–$C_4$-alkylcarbonyl, unsubstituted or halogen-, $C_1$–$C_4$-alkoxy- or phenyl-substituted $C_1$–$C_4$-alkyl, where the phenyl ring for its part may be substituted by halogen, $C_1$–$C_2$-alkyl or $C_1$–$C_2$-alkoxy, unsubstituted or halogen-, $C_1$–$C_4$-alkoxy- or phenyl-substituted $C_1$–$C_4$-alkoxy, where the phenyl ring for its part may be substituted by halogen, $C_1$–$C_2$-alkyl or $C_1$–$C_2$-alkoxy, unsubstituted or halogen-, $C_1$–$C_4$-alkoxy- or phenyl-substituted $C_1$–$C_4$-alkylthio, where the phenyl ring for its part may be substituted by halogen, $C_1$–$C_2$-alkyl or $C_1$–$C_2$-alkoxy, unsubstituted or $C_1$–$C_4$-alkyl- or halogen-substituted $C_2$–$C_6$-alkenyl or $C_2$–$C_6$-alkynyl, unsubstituted or $C_1$–$C_4$-alkyl-$C_1$–$C_4$-alkoxy-, $C_1$–$C_4$-haloalkyl-, $C_1$–$C_4$-haloalkoxy-, halogen-, phenyl-, cyano-, alkoxycarbonyl- or nitro-substituted phenyl or phenoxy, an unsubstituted or $C_1$–$C_4$-alkyl-, $C_1$–$C_4$-alkoxy-, $C_1$–$C_4$-haloalkyl-, $C_1$–$C_4$-haloalkoxy-, halogen-, phenyl-, cyano- or nitro-substituted 5- or 6-membered saturated or unsaturated heterocycle which may contain up to 4 nitrogen atoms and/or up to 2 oxygen or sulfur atoms as ring members, selected from the group consisting of tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, 1,2,4-oxadiazolidinyl, 1,2,4-thiadiazolidinyl, 1,2,4-triazolidinyl, 1,3,4-oxadiazolidinyl, 1,3,4-thiadiazolidinyl, 1,3,4-triazolidinyl, 2,3-dihydrofuranyl, 2,5-dihydrofuranyl, 2,3-dihydrothienyl, 2,5-dihydrothienyl, 2,3-dihydropyrrolyl, 2,5-dihydropyrrolyl, 2,3-dihydroisoxazolyl, 4,5-dihydroisoxazolyl, 2,5-dihydroisoxazolyl, 2,5-dihydroxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, morpholinyl, piperidinyl, tetrahydropyridazinyl, tetrahydropyrimidinyl, tetrahydropyrazinyl, 1,3,5-tetrahydrotriazinyl, 1,2,4-tetrahydrotriazinyl, 1,3-dihydrooxazinyl, 1,3-dithianyl, tetrahydropyranyl, tetrahydrothiopyranyl, 1,3-dioxolanyl, 1,1-dioxo-2,3,4,5-tetrahydrothienyl, 1,3-dihydrooxazinyl, furyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2,4-triazolyl, tetrazolyl, 1,3,4-oxadiazolyl, 1,3,4-thiadiazolyl, 1,3,4-triazolyl, pyridyl, pyridazinyl, pyrimidinyl, pyrazinyl, 1,3,5-triazinyl, 1,2,4-triazinyl, 1,2,4,5-tetrazinyl;

$R^4$ is $C_1$–$C_6$-alkyl, $C_1$–$C_4$-haloalkyl; or $R^3$ and $R^4$ form an unsubstituted or substituted saturated or unsaturated 2- or 3-membered bridge which may contain a sulfur atom which may be oxidized to the sulfoxide or sulfone;

$R^5$ is hydrogen, $C_1$–$C_4$-alkyl which is unsubstituted or substituted by halogen, $C_1$–$C_4$-alkoxy or phenyl, where the phenyl ring may carry one to five substituents selected from the group consisting of halogen, $C_1$–$C_2$-alkyl and $C_1$–$C_2$-alkoxy;

$R^6$ is $C_1$–$C_4$-alkyl which is unsubstituted or substituted by halogen, $C_1$–$C_4$-alkoxy or phenyl, where the phenyl ring may carry one to five substituents selected from the group consisting of halogen, $C_1$–$C_2$-alkyl or $C_1$–$C_2$-alkoxy;

$R^7$ is hydrogen, $C_1$–$C_4$-alkyl or $C_1$–$C_4$-haloalkyl;

n is 0, 1 or 2;

X is hydrogen, chlorine or bromine;

where the compounds claimed may be present both in the trans and in the cis form or as a mixture of these isomers.

Preference is given to phenyl rings and heterocycles which are either unsubstituted or carry one to three halogen atoms and/or one or two radicals selected from the group consisting of: nitro, cyano, methyl, ethyl, trifluoromethyl, methoxy, ethoxy and trifluoromethoxy.

Particular preference is given to the compounds of the formula I of Table 1, where the substituents may have the following meanings, in each case either alone or in combination:

$R^1$ is methyl, ethyl;

$R^2$ is chlorine, methyl, methoxy;

$R^3$ is hydrogen, methyl, unsubstituted benzyl or benzyl which is fluorine-, chlorine-, methyl- or methoxy-substituted in the phenyl moiety, allyl, propyn-3-yl, methoxy, ethoxy, 2-methoxyethoxy, methylthio, methylcarbonyl, methoxycarbonyl, dimethylaminocarbonyl, cyano; preferably unsubstituted or fluorine-, chlorine-, methyl- or methoxy-substituted phenyl, 2-furyl, 3-furyl, 2-thienyl, 3-thienyl, 4,5-dihydroisoxazol-3-yl, isoxazol-5-yl, isoxazol-3-yl, pyrazol-1-yl, pyrazol-5-yl, oxazol-2-yl, 4,5-dihydrooxazol-2-yl, 1,3-dioxolan-2-yl, 1,3-dithiolan-2-yl, thiazol-2-yl, thiazol-5-yl, thiazol-4-yl, [1,2,4]-triazol-1-yl, [1,3,4]-oxadiazol-2-yl, 2-pyridyl, 3-pyridyl, 4-pyridyl, pyrimidin-2-yl, pyrimidin-4-yl, 1,3-dioxan-2-yl, 1,3-dithian-2-yl;

$R^4$ is methyl;

$R^7$ is hydrogen;

n is 2;

X is chlorine.

The benzoylpyrazoles of the formula II in which $R^3$ is an unsubstituted or substituted 5- or 6-membered saturated or unsaturated heterocycle are novel. Benzoylpyrazoles of the formula II which are particularly suitable for use as intermediates for preparing the herbicidally active compounds described in DE Appl. No. 19740494.4 are those where the substituents have the following meanings:

$R^1$ are $C_1$–$C_4$-alkyl or $C_1$–$C_4$-haloalkyl;

$R^2$ is $C_1$–$C_4$-alkyl, $C_1$–$C_4$-haloalkyl, $C_1$–$C_4$-alkoxy, $C_1$–$C_4$-haloalkoxy, halogen;

$R^3$ is an unsubstituted or $C_1$–$C_4$-alkyl-, $C_1$–$C_4$-alkoxy-, $C_1$–$C_4$-haloalkyl-, $C_1$–$C_4$-haloalkoxy- or halogen-substituted 5- or 6-membered saturated or unsaturated heterocycle selected from the group consisting of tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, 1,2,4-oxadiazolidinyl, 1,2,4-thiadiazolidinyl, 1,2,4-triazoldinyl, 1,3,4-oxadiazolidinyl, 1,3,4-thiadiazolidinyl, 1,3,4-triazolidinyl, 2,3-dihydrofuranyl, 2,5-dihydrofuranyl, 2,3-dihydrothienyl, 2,5-dihydrothienyl, 2,3-dihydropyrrolyl, 2,5-dihydropyrrolyl, 2,3-dihydroisoxazolyl, 4,5-dihydroisoxazolyl, 2,5-dihydroisoxazolyl, 2,5-dihydroxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, morpholinyl, piperidinyl, tetrahydropyridazinyl, tetrahydropyrimidinyl, tetrahydropyrazinyl, 1,3,5-tetrahydrotriazinyl, 1,2,4-tetrahydrotriazinyl, 1,3-dihydrooxazinyl, 1,3-dithianyl, tetrahydropyranyl, tetrahydrothiopyranyl, 1,3-dioxolanyl, 1,1-dioxo-2,3,4,5-tetrahydrothienyl, 1,3-dihydrooxazinyl, furyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2,4-triazolyl, tetrazolyl, 1,3,4-oxadiazolyl, 1,3,4-thiadiazolyl, 1,3,4-triazolyl, pyridyl, pyridazinyl, pyrimidinyl, pyrazinyl, 1,3,5-triazinyl, 1,2,4-triazinyl, 1,2,4,5-tetrazinyl, particular preference is given to:

2-furyl, 3-furyl, 2-thienyl, 3-thienyl, 4,5-dihydroisoxazol-3-yl, isoxazol-5-yl, isoxazol-3-yl, pyrazol-1-yl, pyrazol-5-yl, oxazol-2-yl, 4,5-dihydrooxazol-2-yl, 1,3-dioxolan-2-yl, 1,3-dithiolan-2-yl, thiazol-2-yl, thiazol-5-yl, thiazol-4-yl, [1,2,4]-triazol-1-yl, [1,3,4]-oxadiazol-2-yl, 2-pyridyl, 3-pyridyl, 4-pyridyl, pyrimidin-2-yl, pyrimidin-4-yl, 1,3-dioxan-2-yl, 1,3-dithian-2-yl;

$R^4$ is $C_1$–$C_4$-alkyl or $C_1$–$C_4$-haloalkyl;

$R^7$ is hydrogen, $C_1$–$C_4$-alkyl or $C_1$–$C_4$-haloalkyl;

n is 0, 1, 2;

X is chlorine, bromine.

Particular preference is given to the compounds II of Table 2.

PREPARATION EXAMPLES

1) cis-4-[Chloro(2-chloro-3-(4,5-dihydroisoxazol-3-yl)-4-methylsulfonylphenyl)methylene]-2-methyl-2,4-dihydropyrazol-3-one (Tab.1 No. I.20)

5.0 g of (2-chloro-3-(4,5-dihydroisoxazol-3-yl)-4-methylsulfonylphenyl)(5-hydroxy-1-methyl-1H-pyrazol-4-yl)-methanone in 15 ml of toluene were mixed with 2.0 g of phosphorus oxychloride and two drops of dimethylformamide and heated under reflux for 7 h. A further 1.0 g of phosphorus oxychloride were added and the mixture was heated under reflux for a further 7 h. The reaction mixture was then added to 125 ml of ice-water and extracted with methyl tert-butyl ether. The crude product was chromatographed over silica gel using cyclohexane/ethyl acetate/methanol. Yield: 1.3 g of a colorless solid (cis isomer). $^1$H NMR (CDCl$_3$): d=3.27 (s); 3.31 (s); 3.45 (t); 4.57 (t); 7.65 (d); 7.73 (s); 8.15 (d). Additionally, the isomeric benzoylpyrazole was isolated during the chromatographic purification of the reaction mixture:

(5-Chloro-1-methylpyrazol-4-yl)-(2-chloro-3-(4,5-dihydroisoxazol-3-yl)-4-methylsulfonylphenyl)methanone (Tab. 2 No. II.17): $^1$H NMR (CDCl$_3$): d=3.30 (s); 3.45 (t); 3.93 (s), 4.'(t); 7.61 (d); 7.75 (s); 8.17 (d).

2) cis-4-[Chloro(2-chloro-3-(4,5-dihydroisoxazol-3-yl)-4-methylsulfonylphenyl)methylene]-2-ethyl-2,4-dihydropyrazol-3-one (Tab.1 No. I.119)

The compound can be prepared by the method of Example 1. Colorless solid (cis isomer); $^1$H NMR (CDCl$_3$): d=1.28 (t); 3.27 (s) 3.46 (t); 3.72 (q), 4.62 (t); 7.64 (d); 7.73 (s); 8.16 (d).

Additionally, the isomeric benzoylpyrazole was isolated during the chromatographic purification of the reaction mixture:

(5-Chloro-1-ethylpyrazol-4-yl)-(2-chloro-3-(4,5-dihydroisoxazol-3-yl)-4-methylsulfonylphenyl)methanone (Tab. 2 No. II.56): $^1$H NMR (CDCl$_3$): d=1.50 (t); 3.28 (s); 3.45 (t); 4.28 (q), 4.63 (t); 7.63 (d); 7.74 (s); 8.18 (d).

3) cis-4-[Bromo(2-chloro-3-(4,5-dihydroisoxazol-3-yl)-4-methylsulfonylphenyl)methylene]-2-methyl-2,4-dihydropyrazol-3-one (Tab.1 No. 1.466)

2.5 g of (2-chloro-3-(4,5-dihydroisoxazol-3-yl)-4-methylsulfonylphenyl)(5-hydroxy-1-methyl-1H-pyrazol-4-yl)-methanone in 20 ml of toluene were admixed with 1.87 g of phosphorus oxybromide and two drops of dimethylformamide and heated under reflux for 13 h. The reaction mixture was then poured into a 50° C. sodium carbonate solution and extracted with methyl tert-butyl ether. The crude product was chromatographed over silica gel using cyclohexane/ethyl acetate/methanol. $^1$H NMR (CDCl$_3$): d=3.25 (s); 3.31 (s); 3.43 (m); 4.59 (t); 7.57 (d); 7.63 (s); 8.15 (d).

The benzylidenepyrazolones of the formula I and benzoylpyrazoles of the formula II listed in Tables 1 and 2 below can be synthesized by a method similar to the procedures given in the synthesis examples above.

TABLE 1

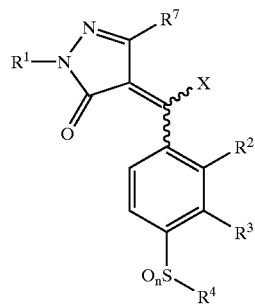

| No. | $R^1$ | $R^2$ | $R^3$ | $R^4$ | $R^7$ | X | n | Isomer | Phys. Data |
|---|---|---|---|---|---|---|---|---|---|
| I.1 | CH$_3$ | Cl | H | CH$_3$ | H | Cl | 2 | cis | |
| I.2 | CH$_3$ | Cl | F | CH$_3$ | H | Cl | 2 | cis | |
| I.3 | CH$_3$ | Cl | Cl | CH$_3$ | H | Cl | 2 | cis | |
| I.4 | CH$_3$ | Cl | Br | CH$_3$ | H | Cl | 2 | cis | |
| I.5 | CH$_3$ | Cl | CH$_3$ | CH$_3$ | H | Cl | 2 | cis | |
| I.6 | CH$_3$ | Cl | CF$_3$ | CH$_3$ | H | Cl | 2 | cis | |
| I.7 | CH$_3$ | Cl | CHF$_2$ | CH$_3$ | H | Cl | 2 | cis | |
| I.8 | CH$_3$ | Cl | ethyl | CH$_3$ | H | Cl | 2 | cis | |
| I.9 | CH$_3$ | Cl | isopropyl | CH$_3$ | H | Cl | 2 | cis | |
| I.10 | CH$_3$ | Cl | benzyl | CH$_3$ | H | Cl | 2 | cis | |
| I.11 | CH$_3$ | Cl | 4-chlorophenylmethyl | CH$_3$ | H | Cl | 2 | cis | |
| I.12 | CH$_3$ | Cl | allyl | CH$_3$ | H | Cl | 2 | cis | |
| I.13 | CH$_3$ | Cl | trans-chloroallyl | CH$_3$ | H | Cl | 2 | cis | |
| I.14 | CH$_3$ | Cl | cis-chloroallyl | CH$_3$ | H | Cl | 2 | cis | |

TABLE 1-continued

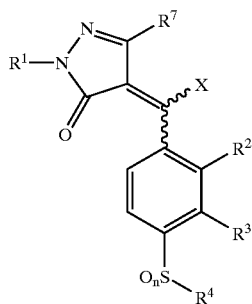

| No. | $R^1$ | $R^2$ | $R^3$ | $R^4$ | $R^7$ | X | n | Isomer | Phys. Data |
|---|---|---|---|---|---|---|---|---|---|
| I.15 | $CH_3$ | Cl | cis-2-chlorovinyl | $CH_3$ | H | Cl | 2 | cis | |
| I.16 | $CH_3$ | Cl | trans-2-chlorovinyl | $CH_3$ | H | Cl | 2 | cis | |
| I.17 | $CH_3$ | Cl | 2,2-dichlorovinyl | $CH_3$ | H | Cl | 2 | cis | |
| I.18 | $CH_3$ | Cl | propyn-3-yl | $CH_3$ | H | Cl | 2 | cis | |
| I.19 | $CH_3$ | Cl | ethynyl | $CH_3$ | H | Cl | 2 | cis | |
| I.20 | $CH_3$ | Cl | 4,5-dihydroisoxazol-3-yl | $CH_3$ | H | Cl | 2 | cis | see Example 1 |
| I.21 | $CH_3$ | Cl | isoxazol-3-yl | $CH_3$ | H | Cl | 2 | cis | |
| I.22 | $CH_3$ | Cl | 3-methylisoxazol-5-yl | $CH_3$ | H | Cl | 2 | cis | |
| I.23 | $CH_3$ | Cl | 4-methyl-4,5-dihydroisoxazol-3-yl | $CH_3$ | H | Cl | 2 | cis | |
| I.24 | $CH_3$ | Cl | 3-ethyl-4,5-dihydroisoxazol-4-yl | $CH_3$ | H | Cl | 2 | cis | |
| I.25 | $CH_3$ | Cl | 3-ethyl-4,5-dihydroisoxazol-5-yl | $CH_3$ | H | Cl | 2 | cis | |
| I.26 | $CH_3$ | Cl | 5-methyl-4,5-dihydroisoxazol-3-yl | $CH_3$ | H | Cl | 2 | cis | |
| I.27 | $CH_3$ | Cl | 4,5-dimethyl-4,5-dihydroisoxazol-3-yl | $CH_3$ | H | Cl | 2 | cis | |
| I.28 | $CH_3$ | Cl | thiazol-2-yl | $CH_3$ | H | Cl | 2 | cis | |
| I.29 | $CH_3$ | Cl | 5-methylthiazol-2-yl | $CH_3$ | H | Cl | 2 | cis | |
| I.30 | $CH_3$ | Cl | thiazol-4-yl | $CH_3$ | H | Cl | 2 | cis | |
| I.31 | $CH_3$ | Cl | thiazol-5-yl | $CH_3$ | H | Cl | 2 | cis | |
| I.32 | $CH_3$ | Cl | oxazol-2-yl | $CH_3$ | H | Cl | 2 | cis | |
| I.33 | $CH_3$ | Cl | 4,5-dihydrooxazol-2-yl | $CH_3$ | H | Cl | 2 | cis | |
| I.34 | $CH_3$ | Cl | pyrrol-1-yl | $CH_3$ | H | Cl | 2 | cis | |
| I.35 | $CH_3$ | Cl | pyrazol-1-yl | $CH_3$ | H | Cl | 2 | cis | |
| I.36 | $CH_3$ | Cl | 1-methylpyrazol-5-yl | $CH_3$ | H | Cl | 2 | cis | |
| I.37 | $CH_3$ | Cl | 1-methylpyrazol-3-yl | $CH_3$ | H | Cl | 2 | cis | |
| I.38 | $CH_3$ | Cl | 1-methoxypyrazol-5-yl | $CH_3$ | H | Cl | 2 | cis | |
| I.39 | $CH_3$ | Cl | 1-methoxypyrazol-3-yl | $CH_3$ | H | Cl | 2 | cis | |
| I.40 | $CH_3$ | Cl | 1-methylimidazol-2-yl | $CH_3$ | H | Cl | 2 | cis | |
| I.41 | $CH_3$ | Cl | imidazol-1-yl | $CH_3$ | H | Cl | 2 | cis | |
| I.42 | $CH_3$ | Cl | [1,2,4]-triazol-1-yl | $CH_3$ | H | Cl | 2 | cis | |
| I.43 | $CH_3$ | Cl | 1-methyl-[1,2,4]-triazol-3-yl | $CH_3$ | H | Cl | 2 | cis | |
| I.44 | $CH_3$ | Cl | 2-thienyl | $CH_3$ | H | Cl | 2 | cis | |
| I.45 | $CH_3$ | Cl | 3-thienyl | $CH_3$ | H | Cl | 2 | cis | |
| I.46 | $CH_3$ | Cl | tetrahydrothiopyran-3-yl | $CH_3$ | H | Cl | 2 | cis | |
| I.47 | $CH_3$ | Cl | tetrahydrothiopyran-4-yl | $CH_3$ | H | Cl | 2 | cis | |
| I.48 | $CH_3$ | Cl | [1,3]dithiolan-2-yl | $CH_3$ | H | Cl | 2 | cis | |
| I.49 | $CH_3$ | Cl | 2-furyl | $CH_3$ | H | Cl | 2 | cis | |
| I.50 | $CH_3$ | Cl | 3-furyl | $CH_3$ | H | Cl | 2 | cis | |
| I.51 | $CH_3$ | Cl | tetrahydrofuran-2-yl | $CH_3$ | H | Cl | 2 | cis | |
| I.52 | $CH_3$ | Cl | tetrahydrofuran-3-yl | $CH_3$ | H | Cl | 2 | cis | |
| I.53 | $CH_3$ | Cl | [1,3]dioxolan-2-yl | $CH_3$ | H | Cl | 2 | cis | |
| I.54 | $CH_3$ | Cl | tetrahydropyran-3-yl | $CH_3$ | H | Cl | 2 | cis | |
| I.55 | $CH_3$ | Cl | tetrahydropyran-4-yl | $CH_3$ | H | Cl | 2 | cis | |
| I.56 | $CH_3$ | Cl | [1,3]dioxan-2-yl | $CH_3$ | H | Cl | 2 | cis | |
| I.57 | $CH_3$ | Cl | [1,3,4]-oxadiazol-2-yl | $CH_3$ | H | Cl | 2 | cis | |
| I.58 | $CH_3$ | Cl | piperidin-1-yl | $CH_3$ | H | Cl | 2 | cis | |
| I.59 | $CH_3$ | Cl | 2-pyridyl | $CH_3$ | H | Cl | 2 | cis | |
| I.60 | $CH_3$ | Cl | 6-methoxy-2-pyridyl | $CH_3$ | H | Cl | 2 | cis | |
| I.61 | $CH_3$ | Cl | 5-trifluoromethyl-2-pyridyl | $CH_3$ | H | Cl | 2 | cis | |
| I.62 | $CH_3$ | Cl | 2-chloro-5-trifluoromethyl-2-pyridyl | $CH_3$ | H | Cl | 2 | cis | |
| I.63 | $CH_3$ | Cl | 3-pyridyl | $CH_3$ | H | Cl | 2 | cis | |
| I.64 | $CH_3$ | Cl | 4-pyridyl | $CH_3$ | H | Cl | 2 | cis | |
| I.65 | $CH_3$ | Cl | morpholin-4-yl | $CH_3$ | H | Cl | 2 | cis | |
| I.66 | $CH_3$ | Cl | pyrimidin-2-yl | $CH_3$ | H | Cl | 2 | cis | |
| I.67 | $CH_3$ | Cl | pyrimidin-4-yl | $CH_3$ | H | Cl | 2 | cis | |
| I.68 | $CH_3$ | Cl | pyrazin-2-yl | $CH_3$ | H | Cl | 2 | cis | |
| I.69 | $CH_3$ | Cl | pyridazin-3-yl | $CH_3$ | H | Cl | 2 | cis | |
| I.70 | $CH_3$ | Cl | pyridazin-4-yl | $CH_3$ | H | Cl | 2 | cis | |
| I.71 | $CH_3$ | Cl | 6-methylpyridazin-3-yl | $CH_3$ | H | Cl | 2 | cis | |
| I.72 | $CH_3$ | Cl | 6-methoxypyridazin-3-yl | $CH_3$ | H | Cl | 2 | cis | |
| I.73 | $CH_3$ | Cl | [1,3,5]-triazin-2-yl | $CH_3$ | H | Cl | 2 | cis | |
| I.74 | $CH_3$ | Cl | [1,2,4]-triazin-3-yl | $CH_3$ | H | Cl | 2 | cis | |
| I.75 | $CH_3$ | Cl | phenyl | $CH_3$ | H | Cl | 2 | cis | |

TABLE 1-continued

| No. | R¹ | R² | R³ | R⁴ | R⁷ | X | n | Isomer | Phys. Data |
|---|---|---|---|---|---|---|---|---|---|
| I.76 | CH₃ | Cl | 2-fluorophenyl | CH₃ | H | Cl | 2 | cis | |
| I.77 | CH₃ | Cl | 3-trifluoromethylphenyl | CH₃ | H | Cl | 2 | cis | |
| I.78 | CH₃ | Cl | 2-methylphenyl | CH₃ | H | Cl | 2 | cis | |
| I.79 | CH₃ | Cl | 3-methylphenyl | CH₃ | H | Cl | 2 | cis | |
| I.80 | CH₃ | Cl | 4-methylphenyl | CH₃ | H | Cl | 2 | cis | |
| I.81 | CH₃ | Cl | 4-chlorophenyl | CH₃ | H | Cl | 2 | cis | |
| I.82 | CH₃ | Cl | 2-chlorophenyl | CH₃ | H | Cl | 2 | cis | |
| I.83 | CH₃ | Cl | 3-chlorophenyl | CH₃ | H | Cl | 2 | cis | |
| I.84 | CH₃ | Cl | 4-methoxyphenyl | CH₃ | H | Cl | 2 | cis | |
| I.85 | CH₃ | Cl | methylthio | CH₃ | H | Cl | 2 | cis | |
| I.86 | CH₃ | Cl | methoxy | CH₃ | H | Cl | 2 | cis | |
| I.87 | CH₃ | Cl | ethoxy | CH₃ | H | Cl | 2 | cis | |
| I.88 | CH₃ | Cl | 2-methoxyethoxy | CH₃ | H | Cl | 2 | cis | |
| I.89 | CH₃ | Cl | formyl | CH₃ | H | Cl | 2 | cis | |
| I.90 | CH₃ | Cl | acetylamino | CH₃ | H | Cl | 2 | cis | |
| I.91 | CH₃ | Cl | methylcarbonyl | CH₃ | H | Cl | 2 | cis | |
| I.92 | CH₃ | Cl | methoxycarbonyl | CH₃ | H | Cl | 2 | cis | |
| I.93 | CH₃ | Cl | dimethylaminocarbonyl | CH₃ | H | Cl | 2 | cis | |
| I.94 | CH₃ | Cl | methoxyiminomethyl | CH₃ | H | Cl | 2 | cis | |
| I.95 | CH₃ | Cl | ethoxyiminomethyl | CH₃ | H | Cl | 2 | cis | |
| I.96 | CH₃ | Cl | 1-ethoxyiminoethyl | CH₃ | H | Cl | 2 | cis | |
| I.97 | CH₃ | Cl | 1-methoxyiminoethyl | CH₃ | H | Cl | 2 | cis | |
| I.98 | CH₃ | Cl | 1-ethoxyiminopropyl | CH₃ | H | Cl | 2 | cis | |
| I.99 | CH₃ | Cl | 1-methoxyiminopropyl | CH₃ | H | Cl | 2 | cis | |
| I.100 | CH₃ | Cl | cyano | CH₃ | H | Cl | 2 | cis | |
| I.101 | C₂H₅ | Cl | H | CH₃ | H | Cl | 2 | cis | |
| I.102 | C₂H₅ | Cl | Cl | CH₃ | H | Cl | 2 | cis | |
| I.103 | C₂H₅ | Cl | Br | CH₃ | H | Cl | 2 | cis | |
| I.104 | C₂H₅ | Cl | CH₃ | CH₃ | H | Cl | 2 | cis | |
| I.105 | C₂H₅ | Cl | CF₃ | CH₃ | H | Cl | 2 | cis | |
| I.106 | C₂H₅ | Cl | CHF₂ | CH₃ | H | Cl | 2 | cis | |
| I.107 | C₂H₅ | Cl | ethyl | CH₃ | H | Cl | 2 | cis | |
| I.108 | C₂H₅ | Cl | isopropyl | CH₃ | H | Cl | 2 | cis | |
| I.109 | C₂H₅ | Cl | benzyl | CH₃ | H | Cl | 2 | cis | |
| I.110 | C₂H₅ | Cl | 4-chlorophenylmethyl | CH₃ | H | Cl | 2 | cis | |
| I.111 | C₂H₅ | Cl | allyl | CH₃ | H | Cl | 2 | cis | |
| I.112 | C₂H₅ | Cl | trans-chloroallyl | CH₃ | H | Cl | 2 | cis | |
| I.113 | C₂H₅ | Cl | cis-chloroallyl | CH₃ | H | Cl | 2 | cis | |
| I.114 | C₂H₅ | Cl | cis-2-chlorovinyl | CH₃ | H | Cl | 2 | cis | |
| I.115 | C₂H₅ | Cl | trans-2-chlorovinyl | CH₃ | H | Cl | 2 | cis | |
| I.116 | C₂H₅ | Cl | 2,2-dichlorovinyl | CH₃ | H | Cl | 2 | cis | |
| I.117 | C₂H₅ | Cl | propyn-3-yl | CH₃ | H | Cl | 2 | cis | |
| I.118 | C₂H₅ | Cl | ethynyl | CH₃ | H | Cl | 2 | cis | |
| I.119 | C₂H₅ | Cl | 4,5-dihydroisoxazol-3-yl | CH₃ | H | Cl | 2 | cis | see Example 2 |
| I.120 | C₂H₅ | Cl | isoxazol-3-yl | CH₃ | H | Cl | 2 | cis | |
| I.121 | C₂H₅ | Cl | 3-methylisoxazol-5-yl | CH₃ | H | Cl | 2 | cis | |
| I.122 | C₂H₅ | Cl | 4-methyl-4,5-dihydroisoxazol-3-yl | CH₃ | H | Cl | 2 | cis | |
| I.123 | C₂H₅ | Cl | 3-ethyl-4,5-dihydroisoxazol-4-yl | CH₃ | H | Cl | 2 | cis | |
| I.124 | C₂H₅ | Cl | 3-ethyl-4,5-dihydroisoxazol-5-yl | CH₃ | H | Cl | 2 | cis | |
| I.125 | C₂H₅ | Cl | 5-methyl-4,5-dihydroisoxazol-3-yl | CH₃ | H | Cl | 2 | cis | |
| I.126 | C₂H₅ | Cl | 4,5-dimethyl-4,5-dihydroisoxazol-3-yl | CH₃ | H | Cl | 2 | cis | |
| I.127 | C₂H₅ | Cl | thiazol-2-yl | CH₃ | H | Cl | 2 | cis | |
| I.128 | C₂H₅ | Cl | 5-methylthiazol-2-yl | CH₃ | H | Cl | 2 | cis | |
| I.129 | C₂H₅ | Cl | thiazol-4-yl | CH₃ | H | Cl | 2 | cis | |
| I.130 | C₂H₅ | Cl | thiazol-5-yl | CH₃ | H | Cl | 2 | cis | |
| I.131 | C₂H₅ | Cl | oxazol-2-yl | CH₃ | H | Cl | 2 | cis | |
| I.132 | C₂H₅ | Cl | 4,5-dihydrooxazol-2-yl | CH₃ | H | Cl | 2 | cis | |
| I.133 | C₂H₅ | Cl | pyrrol-1-yl | CH₃ | H | Cl | 2 | cis | |
| I.134 | C₂H₅ | Cl | pyrazol-1-yl | CH₃ | H | Cl | 2 | cis | |
| I.135 | C₂H₅ | Cl | 1-methylpyrazol-5-yl | CH₃ | H | Cl | 2 | cis | |
| I.136 | C₂H₅ | Cl | 1-methylpyrazol-3-yl | CH₃ | H | Cl | 2 | cis | |

TABLE 1-continued

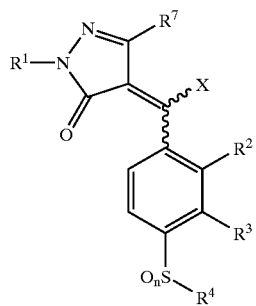

| No. | R¹ | R² | R³ | R⁴ | R⁷ | X | n | Isomer | Phys. Data |
|---|---|---|---|---|---|---|---|---|---|
| I.137 | C₂H₅ | Cl | 1-methoxypyrazol-5-yl | CH₃ | H | Cl | 2 | cis | |
| I.138 | C₂H₅ | Cl | 1-methoxypyrazol-3-yl | CH₃ | H | Cl | 2 | cis | |
| I.139 | C₂H₅ | Cl | 1-methylimidazol-2-yl | CH₃ | H | Cl | 2 | cis | |
| I.140 | C₂H₅ | Cl | imidazol-1-yl | CH₃ | H | Cl | 2 | cis | |
| I.141 | C₂H₅ | Cl | [1,2,4]-triazol-1-yl | CH₃ | H | Cl | 2 | cis | |
| I.142 | C₂H₅ | Cl | 1-methyl-[1,2,4]-triazol-3-yl | CH₃ | H | Cl | 2 | cis | |
| I.143 | C₂H₅ | Cl | 2-thienyl | CH₃ | H | Cl | 2 | cis | |
| I.144 | C₂H₅ | Cl | 3-thienyl | CH₃ | H | Cl | 2 | cis | |
| I.145 | C₂H₅ | Cl | tetrahydrothiopyran-3-yl | CH₃ | H | Cl | 2 | cis | |
| I.146 | C₂H₅ | Cl | tetrahydrothiopyran-4-yl | CH₃ | H | Cl | 2 | cis | |
| I.147 | C₂H₅ | Cl | [1,3]dithiolan-2-yl | CH₃ | H | Cl | 2 | cis | |
| I.148 | C₂H₅ | Cl | 2-furyl | CH₃ | H | Cl | 2 | cis | |
| I.149 | C₂H₅ | Cl | 3-furyl | CH₃ | H | Cl | 2 | cis | |
| I.150 | C₂H₅ | Cl | tetrahydrofuran-2-yl | CH₃ | H | Cl | 2 | cis | |
| I.151 | C₂H₅ | Cl | tetrahydrofuran-3-yl | CH₃ | H | Cl | 2 | cis | |
| I.152 | C₂H₅ | Cl | [1,3]dioxolan-2-yl | CH₃ | H | Cl | 2 | cis | |
| I.153 | C₂H₅ | Cl | tetrahydropyran-3-yl | CH₃ | H | Cl | 2 | cis | |
| I.154 | C₂H₅ | Cl | tetrahydropyran-4-yl | CH₃ | H | Cl | 2 | cis | |
| I.155 | C₂H₅ | Cl | [1,3]dioxan-2-yl | CH₃ | H | Cl | 2 | cis | |
| I.156 | C₂H₅ | Cl | [1,3,4]-oxadiazol-2-yl | CH₃ | H | Cl | 2 | cis | |
| I.157 | C₂H₅ | Cl | piperidin-1-yl | CH₃ | H | Cl | 2 | cis | |
| I.158 | C₂H₅ | Cl | 2-pyridyl | CH₃ | H | Cl | 2 | cis | |
| I.159 | C₂H₅ | Cl | 6-methoxy-2-pyridyl | CH₃ | H | Cl | 2 | cis | |
| I.160 | C₂H₅ | Cl | 5-trifluoromethyl-2-pyridyl | CH₃ | H | Cl | 2 | cis | |
| I.161 | C₂H₅ | Cl | 2-chloro-5-trifluoromethyl-2-pyridyl | CH₃ | H | Cl | 2 | cis | |
| I.162 | C₂H₅ | Cl | 3-pyridyl | CH₃ | H | Cl | 2 | cis | |
| I.163 | C₂H₅ | Cl | 4-pyridyl | CH₃ | H | Cl | 2 | cis | |
| I.164 | C₂H₅ | Cl | morpholin-4-yl | CH₃ | H | Cl | 2 | cis | |
| I.165 | C₂H₅ | Cl | pyrimidin-2-yl | CH₃ | H | Cl | 2 | cis | |
| I.166 | C₂H₅ | Cl | pyrimidin-4-yl | CH₃ | H | Cl | 2 | cis | |
| I.167 | C₂H₅ | Cl | pyrazin-2-yl | CH₃ | H | Cl | 2 | cis | |
| I.168 | C₂H₅ | Cl | pyridazin-3-yl | CH₃ | H | Cl | 2 | cis | |
| I.169 | C₂H₅ | Cl | pyridazin-4-yl | CH₃ | H | Cl | 2 | cis | |
| I.170 | C₂H₅ | Cl | 6-methylpyridazin-3-yl | CH₃ | H | Cl | 2 | cis | |
| I.171 | C₂H₅ | Cl | 6-methoxypyridazin-3-yl | CH₃ | H | Cl | 2 | cis | |
| I.172 | C₂H₅ | Cl | [1,3,5]-triazin-2-yl | CH₃ | H | Cl | 2 | cis | |
| I.173 | C₂H₅ | Cl | [1,2,4]-triazin-3-yl | CH₃ | H | Cl | 2 | cis | |
| I.174 | C₂H₅ | Cl | phenyl | CH₃ | H | Cl | 2 | cis | |
| I.175 | C₂H₅ | Cl | 2-fluorophenyl | CH₃ | H | Cl | 2 | cis | |
| I.176 | C₂H₅ | Cl | 3-trifluoromethylphenyl | CH₃ | H | Cl | 2 | cis | |
| I.177 | C₂H₅ | Cl | 2-methylphenyl | CH₃ | H | Cl | 2 | cis | |
| I.178 | C₂H₅ | Cl | 3-methylphenyl | CH₃ | H | Cl | 2 | cis | |
| I.179 | C₂H₅ | Cl | 4-methylphenyl | CH₃ | H | Cl | 2 | cis | |
| I.180 | C₂H₅ | Cl | 4-chlorophenyl | CH₃ | H | Cl | 2 | cis | |
| I.181 | C₂H₅ | Cl | 2-chlorophenyl | CH₃ | H | Cl | 2 | cis | |
| I.182 | C₂H₅ | Cl | 3-chlorophenyl | CH₃ | H | Cl | 2 | cis | |
| I.183 | C₂H₅ | Cl | 4-methoxyphenyl | CH₃ | H | Cl | 2 | cis | |
| I.184 | C₂H₅ | Cl | methylthio | CH₃ | H | Cl | 2 | cis | |
| I.185 | C₂H₅ | Cl | methoxy | CH₃ | H | Cl | 2 | cis | |
| I.186 | C₂H₅ | Cl | ethoxy | CH₃ | H | Cl | 2 | cis | |
| I.187 | C₂H₅ | Cl | 2-methoxyethoxy | CH₃ | H | Cl | 2 | cis | |
| I.188 | C₂H₅ | Cl | formyl | CH₃ | H | Cl | 2 | cis | |
| I.189 | C₂H₅ | Cl | acetylamino | CH₃ | H | Cl | 2 | cis | |
| I.190 | C₂H₅ | Cl | methylcarbonyl | CH₃ | H | Cl | 2 | cis | |
| I.191 | C₂H₅ | Cl | methoxycarbonyl | CH₃ | H | Cl | 2 | cis | |
| I.192 | C₂H₅ | Cl | dimethylaminocarbonyl | CH₃ | H | Cl | 2 | cis | |
| I.193 | C₂H₅ | Cl | methoxyiminomethyl | CH₃ | H | Cl | 2 | cis | |
| I.194 | C₂H₅ | Cl | ethoxyiminomethyl | CH₃ | H | Cl | 2 | cis | |
| I.195 | C₂H₅ | Cl | 1-ethoxyiminoethyl | CH₃ | H | Cl | 2 | cis | |
| I.196 | C₂H₅ | Cl | 1-methoxyiminoethyl | CH₃ | H | Cl | 2 | cis | |
| I.197 | C₂H₅ | Cl | 1-ethoxyiminopropyl | CH₃ | H | Cl | 2 | cis | |

TABLE 1-continued

Structure: pyrazole with R¹-N, R⁷, X, linked to phenyl with R², R³, and O$_n$S-R⁴

| No. | R¹ | R² | R³ | R⁴ | R⁷ | X | n | Isomer | Phys. Data |
|---|---|---|---|---|---|---|---|---|---|
| I.198 | C₂H₅ | Cl | 1-methoxyiminopropyl | CH₃ | H | Cl | 2 | cis | |
| I.199 | C₂H₅ | Cl | cyano | CH₃ | H | Cl | 2 | cis | |
| I.200 | CH₃ | CH₃ | H | CH₃ | H | Cl | 2 | cis | |
| I.201 | CH₃ | CH₃ | F | CH₃ | H | Cl | 2 | cis | |
| I.202 | CH₃ | CH₃ | Cl | CH₃ | H | Cl | 2 | cis | |
| I.203 | CH₃ | CH₃ | Br | CH₃ | H | Cl | 2 | cis | |
| I.204 | CH₃ | CH₃ | CH₃ | CH₃ | H | Cl | 2 | cis | |
| I.205 | CH₃ | CH₃ | CF₃ | CH₃ | H | Cl | 2 | cis | |
| I.206 | CH₃ | CH₃ | CHF₂ | CH₃ | H | Cl | 2 | cis | |
| I.207 | CH₃ | CH₃ | ethyl | CH₃ | H | Cl | 2 | cis | |
| I.208 | CH₃ | CH₃ | isopropyl | CH₃ | H | Cl | 2 | cis | |
| I.209 | CH₃ | CH₃ | benzyl | CH₃ | H | Cl | 2 | cis | |
| I.210 | CH₃ | CH₃ | 4-chlorophenylmethyl | CH₃ | H | Cl | 2 | cis | |
| I.211 | CH₃ | CH₃ | allyl | CH₃ | H | Cl | 2 | cis | |
| I.212 | CH₃ | CH₃ | trans-chloroallyl | CH₃ | H | Cl | 2 | cis | |
| I.213 | CH₃ | CH₃ | cis-chloroallyl | CH₃ | H | Cl | 2 | cis | |
| I.214 | CH₃ | CH₃ | cis-2-chlorovinyl | CH₃ | H | Cl | 2 | cis | |
| I.215 | CH₃ | CH₃ | trans-2-chlorovinyl | CH₃ | H | Cl | 2 | cis | |
| I.216 | CH₃ | CH₃ | 2,2-dichlorovinyl | CH₃ | H | Cl | 2 | cis | |
| I.217 | CH₃ | CH₃ | propyn-3-yl | CH₃ | H | Cl | 2 | cis | |
| I.218 | CH₃ | CH₃ | ethynyl | CH₃ | H | Cl | 2 | cis | |
| I.219 | CH₃ | CH₃ | 4,5-dihydroisoxazol-3-yl | CH₃ | H | Cl | 2 | cis | |
| I.220 | CH₃ | CH₃ | isoxazol-3-yl | CH₃ | H | Cl | 2 | cis | |
| I.221 | CH₃ | CH₃ | 3-methylisoxazol-5-yl | CH₃ | H | Cl | 2 | cis | |
| I.222 | CH₃ | CH₃ | 4-methyl-4,5-dihydroisoxazol-3-yl | CH₃ | H | Cl | 2 | cis | |
| I.223 | CH₃ | CH₃ | 3-ethyl-4,5-dihydroisoxazol-4-yl | CH₃ | H | Cl | 2 | cis | |
| I.224 | CH₃ | CH₃ | 3-ethyl-4,5-dihydrosoxazol-5-yl | CH₃ | H | Cl | 2 | cis | |
| I.225 | CH₃ | CH₃ | 5-methyl-4,5-dihydroisoxazol-3-yl | CH₃ | H | Cl | 2 | cis | |
| I.226 | CH₃ | CH₃ | 4,5-dimethyl-4,5-dihydroisoxazol-3-yl | CH₃ | H | Cl | 2 | cis | |
| I.227 | CH₃ | CH₃ | thiazol-2-yl | CH₃ | H | Cl | 2 | cis | |
| I.228 | CH₃ | CH₃ | 5-methylthiazol-2-yl | CH₃ | H | Cl | 2 | cis | |
| I.229 | CH₃ | CH₃ | thiazol-4-yl | CH₃ | H | Cl | 2 | cis | |
| I.230 | CH₃ | CH₃ | thiazol-5-yl | CH₃ | H | Cl | 2 | cis | |
| I.231 | CH₃ | CH₃ | oxazol-2-yl | CH₃ | H | Cl | 2 | cis | |
| I.232 | CH₃ | CH₃ | 4,5-dihydrooxazol-2-yl | CH₃ | H | Cl | 2 | cis | |
| I.233 | CH₃ | CH₃ | pyrrol-1-yl | CH₃ | H | Cl | 2 | cis | |
| I.234 | CH₃ | CH₃ | pyrazol-1-yl | CH₃ | H | Cl | 2 | cis | |
| I.235 | CH₃ | CH₃ | 1-methylpyrazol-5-yl | CH₃ | H | Cl | 2 | cis | |
| I.236 | CH₃ | CH₃ | 1-methylpyrazol-3-yl | CH₃ | H | Cl | 2 | cis | |
| I.237 | CH₃ | CH₃ | 1-methoxypyrazol-5-yl | CH₃ | H | Cl | 2 | cis | |
| I.238 | CH₃ | CH₃ | 1-methoxypyrazol-3-yl | CH₃ | H | Cl | 2 | cis | |
| I.239 | CH₃ | CH₃ | 1-methylimidazol-2-yl | CH₃ | H | Cl | 2 | cis | |
| I.240 | CH₃ | CH₃ | imidazol-1-yl | CH₃ | H | Cl | 2 | cis | |
| I.241 | CH₃ | CH₃ | [1,2,4]-triazol-1-yl | CH₃ | H | Cl | 2 | cis | |
| I.242 | CH₃ | CH₃ | 1-methyl-[1,2,4]-triazol-3-yl | CH₃ | H | Cl | 2 | cis | |
| I.243 | CH₃ | CH₃ | 2-thienyl | CH₃ | H | Cl | 2 | cis | |
| I.244 | CH₃ | CH₃ | 3-thienyl | CH₃ | H | Cl | 2 | cis | |
| I.245 | CH₃ | CH₃ | tetrahydrothiopyran-3-yl | CH₃ | H | Cl | 2 | cis | |
| I.246 | CH₃ | CH₃ | tetrahydrothiopyran-4-yl | CH₃ | H | Cl | 2 | cis | |
| I.247 | CH₃ | CH₃ | [1,3]dithiolan-2-yl | CH₃ | H | Cl | 2 | cis | |
| I.248 | CH₃ | CH₃ | 2-furyl | CH₃ | H | Cl | 2 | cis | |
| I.249 | CH₃ | CH₃ | 3-furyl | CH₃ | H | Cl | 2 | cis | |
| I.250 | CH₃ | CH₃ | tetrahydrofuran-2-yl | CH₃ | H | Cl | 2 | cis | |
| I.251 | CH₃ | CH₃ | tetrahydrofuran-3-yl | CH₃ | H | Cl | 2 | cis | |
| I.252 | CH₃ | CH₃ | [1,3]dioxolan-2-yl | CH₃ | H | Cl | 2 | cis | |
| I.253 | CH₃ | CH₃ | tetrahydropyran-3-yl | CH₃ | H | Cl | 2 | cis | |
| I.254 | CH₃ | CH₃ | tetrahydropyran-4-yl | CH₃ | H | Cl | 2 | cis | |
| I.255 | CH₃ | CH₃ | [1,3]dioxan-2-yl | CH₃ | H | Cl | 2 | cis | |
| I.256 | CH₃ | CH₃ | [1,3,4]-oxadiazol-2-yl | CH₃ | H | Cl | 2 | cis | |
| I.257 | CH₃ | CH₃ | piperidin-1-yl | CH₃ | H | Cl | 2 | cis | |
| I.258 | CH₃ | CH₃ | 2-pyridyl | CH₃ | H | Cl | 2 | cis | |

TABLE 1-continued

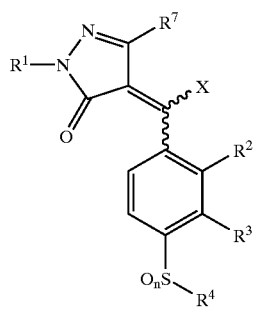

| No. | R¹ | R² | R³ | R⁴ | R⁷ | X | n | Isomer | Phys. Data |
|---|---|---|---|---|---|---|---|---|---|
| I.259 | CH₃ | CH₃ | 6-methoxy-2-pyridyl | CH₃ | H | Cl | 2 | cis | |
| I.260 | CH₃ | CH₃ | 5-trifluoromethyl-2-pyridyl | CH₃ | H | Cl | 2 | cis | |
| I.261 | CH₃ | CH₃ | 2-chloro-5-trifluoromethyl-2-pyridyl | CH₃ | H | Cl | 2 | cis | |
| I.262 | CH₃ | CH₃ | 3-pyridyl | CH₃ | H | Cl | 2 | cis | |
| I.263 | CH₃ | CH₃ | 4-pyridyl | CH₃ | H | Cl | 2 | cis | |
| I.264 | CH₃ | CH₃ | morpholin-4-yl | CH₃ | H | Cl | 2 | cis | |
| I.265 | CH₃ | CH₃ | pyrimidin-2-yl | CH₃ | H | Cl | 2 | cis | |
| I.266 | CH₃ | CH₃ | pyrimidin-4-yl | CH₃ | H | Cl | 2 | cis | |
| I.267 | CH₃ | CH₃ | pyrazin-2-yl | CH₃ | H | Cl | 2 | cis | |
| I.268 | CH₃ | CH₃ | pyridazin-3-yl | CH₃ | H | Cl | 2 | cis | |
| I.269 | CH₃ | CH₃ | pyridazin-4-yl | CH₃ | H | Cl | 2 | cis | |
| I.270 | CH₃ | CH₃ | 6-methylpyridazin-3-yl | CH₃ | H | Cl | 2 | cis | |
| I.271 | CH₃ | CH₃ | 6-methoxypyridazin-3-yl | CH₃ | H | Cl | 2 | cis | |
| I.272 | CH₃ | CH₃ | [1,3,5]-triazin-2-yl | CH₃ | H | Cl | 2 | cis | |
| I.273 | CH₃ | CH₃ | [1,2,4]-triazin-3-yl | CH₃ | H | Cl | 2 | cis | |
| I.274 | CH₃ | CH₃ | phenyl | CH₃ | H | Cl | 2 | cis | |
| I.275 | CH₃ | CH₃ | 2-fluorophenyl | CH₃ | H | Cl | 2 | cis | |
| I.276 | CH₃ | CH₃ | 3-trifluoromethylphenyl | CH₃ | H | Cl | 2 | cis | |
| I.277 | CH₃ | CH₃ | 2-methylphenyl | CH₃ | H | Cl | 2 | cis | |
| I.278 | CH₃ | CH₃ | 3-methylphenyl | CH₃ | H | Cl | 2 | cis | |
| I.279 | CH₃ | CH₃ | 4-methylphenyl | CH₃ | H | Cl | 2 | cis | |
| I.280 | CH₃ | CH₃ | 4-chlorophenyl | CH₃ | H | Cl | 2 | cis | |
| I.281 | CH₃ | CH₃ | 2-chlorophenyl | CH₃ | H | Cl | 2 | cis | |
| I.282 | CH₃ | CH₃ | 3-chlorophenyl | CH₃ | H | Cl | 2 | cis | |
| I.283 | CH₃ | CH₃ | 4-methoxyphenyl | CH₃ | H | Cl | 2 | cis | |
| I.284 | CH₃ | CH₃ | methylthio | CH₃ | H | Cl | 2 | cis | |
| I.285 | CH₃ | CH₃ | methoxy | CH₃ | H | Cl | 2 | cis | |
| I.286 | CH₃ | CH₃ | ethoxy | CH₃ | H | Cl | 2 | cis | |
| I.287 | CH₃ | CH₃ | 2-methoxyethoxy | CH₃ | H | Cl | 2 | cis | |
| I.288 | CH₃ | CH₃ | formyl | CH₃ | H | Cl | 2 | cis | |
| I.289 | CH₃ | CH₃ | acetylamino | CH₃ | H | Cl | 2 | cis | |
| I.290 | CH₃ | CH₃ | methylcarbonyl | CH₃ | H | Cl | 2 | cis | |
| I.291 | CH₃ | CH₃ | methoxycarbonyl | CH₃ | H | Cl | 2 | cis | |
| I.292 | CH₃ | CH₃ | dimethylaminocarbonyl | CH₃ | H | Cl | 2 | cis | |
| I.293 | CH₃ | CH₃ | methoxyiminomethyl | CH₃ | H | Cl | 2 | cis | |
| I.294 | CH₃ | CH₃ | ethoxyiminomethyl | CH₃ | H | Cl | 2 | cis | |
| I.295 | CH₃ | CH₃ | 1-ethoxyiminoethyl | CH₃ | H | Cl | 2 | cis | |
| I.296 | CH₃ | CH₃ | 1-methoxyiminoethyl | CH₃ | H | Cl | 2 | cis | |
| I.297 | CH₃ | CH₃ | 1-ethoxyiminopropyl | CH₃ | H | Cl | 2 | cis | |
| I.298 | CH₃ | CH₃ | 1-methoxyiminopropyl | CH₃ | H | Cl | 2 | cis | |
| I.299 | CH₃ | CH₃ | cyano | CH₃ | H | Cl | 2 | cis | |
| I.300 | C₂H₅ | CH₃ | H | CH₃ | H | Cl | 2 | cis | |
| I.301 | C₂H₅ | CH₃ | F | CH₃ | H | Cl | 2 | cis | |
| I.302 | C₂H₅ | CH₃ | Cl | CH₃ | H | Cl | 2 | cis | |
| I.303 | C₂H₅ | CH₃ | Br | CH₃ | H | Cl | 2 | cis | |
| I.304 | C₂H₅ | CH₃ | CH₃ | CH₃ | H | Cl | 2 | cis | |
| I.305 | C₂H₅ | CH₃ | CF₃ | CH₃ | H | Cl | 2 | cis | |
| I.306 | C₂H₅ | CH₃ | CHF₂ | CH₃ | H | Cl | 2 | cis | |
| I.307 | C₂H₅ | CH₃ | ethyl | CH₃ | H | Cl | 2 | cis | |
| I.308 | C₂H₅ | CH₃ | isopropyl | CH₃ | H | Cl | 2 | cis | |
| I.309 | C₂H₅ | CH₃ | benzyl | CH₃ | H | Cl | 2 | cis | |
| I.310 | C₂H₅ | CH₃ | 4-chlorophenylmethyl | CH₃ | H | Cl | 2 | cis | |
| I.311 | C₂H₅ | CH₃ | allyl | CH₃ | H | Cl | 2 | cis | |
| I.312 | C₂H₅ | CH₃ | trans-chloroallyl | CH₃ | H | Cl | 2 | cis | |
| I.313 | C₂H₅ | CH₃ | cis-chloroallyl | CH₃ | H | Cl | 2 | cis | |
| I.314 | C₂H₅ | CH₃ | cis-2-chlorovinyl | CH₃ | H | Cl | 2 | cis | |
| I.315 | C₂H₅ | CH₃ | trans-2-chlorovinyl | CH₃ | H | Cl | 2 | cis | |
| I.316 | C₂H₅ | CH₃ | 2,2-dichlorovinyl | CH₃ | H | Cl | 2 | cis | |
| I.317 | C₂H₅ | CH₃ | propyn-3-yl | CH₃ | H | Cl | 2 | cis | |
| I.318 | C₂H₅ | CH₃ | ethynyl | CH₃ | H | Cl | 2 | cis | |
| I.319 | C₂H₅ | CH₃ | 4,5-dihydroisoxazol-3-yl | CH₃ | H | Cl | 2 | cis | |

TABLE 1-continued

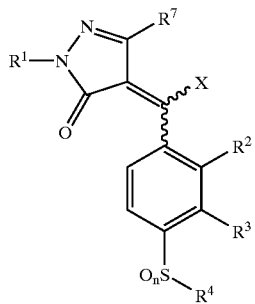

| No. | R¹ | R² | R³ | R⁴ | R⁷ | X | n | Isomer | Phys. Data |
|---|---|---|---|---|---|---|---|---|---|
| I.320 | C₂H₅ | CH₃ | isoxazol-3-yl | CH₃ | H | Cl | 2 | cis | |
| I.321 | C₂H₅ | CH₃ | 3-methylisoxazol-5-yl | CH₃ | H | Cl | 2 | cis | |
| I.322 | C₂H₅ | CH₃ | 4-methyl-4,5-dihydroisoxazol-3-yl | CH₃ | H | Cl | 2 | cis | |
| I.323 | C₂H₅ | CH₃ | 3-ethyl-4,5-dihydroisoxazol-4-yl | CH₃ | H | Cl | 2 | cis | |
| I.324 | C₂H₅ | CH₃ | 3-ethyl-4,5-dihydroisoxazol-5-yl | CH₃ | H | Cl | 2 | cis | |
| I.325 | C₂H₅ | CH₃ | 5-methyl-4,5-dihydroisoxazol-3-yl | CH₃ | H | Cl | 2 | cis | |
| I.326 | C₂H₅ | CH₃ | 4,5-dimethyl-4,5-dihydroisoxazol-3-yl | CH₃ | H | Cl | 2 | cis | |
| I.327 | C₂H₅ | CH₃ | thiazol-2-yl | CH₃ | H | Cl | 2 | cis | |
| I.328 | C₂H₅ | CH₃ | 5-methylthiazol-2-yl | CH₃ | H | Cl | 2 | cis | |
| I.329 | C₂H₅ | CH₃ | thiazol-4-yl | CH₃ | H | Cl | 2 | cis | |
| I.330 | C₂H₅ | CH₃ | thiazol-5-yl | CH₃ | H | Cl | 2 | cis | |
| I.331 | C₂H₅ | CH₃ | oxazol-2-yl | CH₃ | H | Cl | 2 | cis | |
| I.332 | C₂H₅ | CH₃ | 4,5-dihydrooxazol-2-yl | CH₃ | H | Cl | 2 | cis | |
| I.333 | C₂H₅ | CH₃ | pyrrol-1-yl | CH₃ | H | Cl | 2 | cis | |
| I.334 | C₂H₅ | CH₃ | pyrazol-1-yl | CH₃ | H | Cl | 2 | cis | |
| I.335 | C₂H₅ | CH₃ | 1-methylpyrazol-5-yl | CH₃ | H | Cl | 2 | cis | |
| I.336 | C₂H₅ | CH₃ | 1-methylpyrazol-3-yl | CH₃ | H | Cl | 2 | cis | |
| I.337 | C₂H₅ | CH₃ | 1-methoxypyrazol-5-yl | CH₃ | H | Cl | 2 | cis | |
| I.338 | C₂H₅ | CH₃ | 1-methoxypyrazol-3-yl | CH₃ | H | Cl | 2 | cis | |
| I.339 | C₂H₅ | CH₃ | 1-methylimidazol-2-yl | CH₃ | H | Cl | 2 | cis | |
| I.340 | C₂H₅ | CH₃ | imidazol-1-yl | CH₃ | H | Cl | 2 | cis | |
| I.341 | C₂H₅ | CH₃ | [1,2,4]-triazol-1-yl | CH₃ | H | Cl | 2 | cis | |
| I.342 | C₂H₅ | CH₃ | 1-methyl-[1,2,4]-triazol-3-yl | CH₃ | H | Cl | 2 | cis | |
| I.343 | C₂H₅ | CH₃ | 2-thienyl | CH₃ | H | Cl | 2 | cis | |
| I.344 | C₂H₅ | CH₃ | 3-thienyl | CH₃ | H | Cl | 2 | cis | |
| I.345 | C₂H₅ | CH₃ | tetrahydrothiopyran-3-yl | CH₃ | H | Cl | 2 | cis | |
| I.346 | C₂H₅ | CH₃ | tetrahydrothiopyran-4-yl | CH₃ | H | Cl | 2 | cis | |
| I.347 | C₂H₅ | CH₃ | [1,3]dithiolan-2-yl | CH₃ | H | Cl | 2 | cis | |
| I.348 | C₂H₅ | CH₃ | 2-furyl | CH₃ | H | Cl | 2 | cis | |
| I.349 | C₂H₅ | CH₃ | 3-furyl | CH₃ | H | Cl | 2 | cis | |
| I.350 | C₂H₅ | CH₃ | tetrahydrofuran-2-yl | CH₃ | H | Cl | 2 | cis | |
| I.351 | C₂H₅ | CH₃ | tetrahydrofuran-3-yl | CH₃ | H | Cl | 2 | cis | |
| I.352 | C₂H₅ | CH₃ | [1,3]dioxolan-2-yl | CH₃ | H | Cl | 2 | cis | |
| I.353 | C₂H₅ | CH₃ | tetrahydropyran-3-yl | CH₃ | H | Cl | 2 | cis | |
| I.354 | C₂H₅ | CH₃ | tetrahydropyran-4-yl | CH₃ | H | Cl | 2 | cis | |
| I.355 | C₂H₅ | CH₃ | [1,3]dioxan-2-yl | CH₃ | H | Cl | 2 | cis | |
| I.356 | C₂H₅ | CH₃ | [1,3,4]-oxadiazol-2-yl | CH₃ | H | Cl | 2 | cis | |
| I.357 | C₂H₅ | CH₃ | piperidin-1-yl | CH₃ | H | Cl | 2 | cis | |
| I.358 | C₂H₅ | CH₃ | 2-pyridyl | CH₃ | H | Cl | 2 | cis | |
| I.359 | C₂H₅ | CH₃ | 6-methoxy-2-pyridyl | CH₃ | H | Cl | 2 | cis | |
| I.360 | C₂H₅ | CH₃ | 5-trifluoromethyl-2-pyridyl | CH₃ | H | Cl | 2 | cis | |
| I.361 | C₂H₅ | CH₃ | 2-chloro-5-trifluoromethyl-2-pyridyl | CH₃ | H | Cl | 2 | cis | |
| I.362 | C₂H₅ | CH₃ | 3-pyridyl | CH₃ | H | Cl | 2 | cis | |
| I.363 | C₂H₅ | CH₃ | 4-pyridyl | CH₃ | H | Cl | 2 | cis | |
| I.364 | C₂H₅ | CH₃ | morpholin-4-yl | CH₃ | H | Cl | 2 | cis | |
| I.365 | C₂H₅ | CH₃ | pyrimidin-2-yl | CH₃ | H | Cl | 2 | cis | |
| I.366 | C₂H₅ | CH₃ | pyrimidin-4-yl | CH₃ | H | Cl | 2 | cis | |
| I.367 | C₂H₅ | CH₃ | pyrazin-2-yl | CH₃ | H | Cl | 2 | cis | |
| I.368 | C₂H₅ | CH₃ | pyridazin-3-yl | CH₃ | H | Cl | 2 | cis | |
| I.369 | C₂H₅ | CH₃ | pyridazin-4-yl | CH₃ | H | Cl | 2 | cis | |
| I.370 | C₂H₅ | CH₃ | 6-methylpyridazin-3-yl | CH₃ | H | Cl | 2 | cis | |
| I.371 | C₂H₅ | CH₃ | 6-methoxypyridazin-3-yl | CH₃ | H | Cl | 2 | cis | |
| I.372 | C₂H₅ | CH₃ | [1,3,5]-triazin-2-yl | CH₃ | H | Cl | 2 | cis | |
| I.373 | C₂H₅ | CH₃ | [1,2,4]-triazin-3-yl | CH₃ | H | Cl | 2 | cis | |
| I.374 | C₂H₅ | CH₃ | phenyl | CH₃ | H | Cl | 2 | cis | |
| I.375 | C₂H₅ | CH₃ | 2-fluorophenyl | CH₃ | H | Cl | 2 | cis | |
| I.376 | C₂H₅ | CH₃ | 3-trifluoromethylphenyl | CH₃ | H | Cl | 2 | cis | |
| I.377 | C₂H₅ | CH₃ | 2-methylphenyl | CH₃ | H | Cl | 2 | cis | |
| I.378 | C₂H₅ | CH₃ | 3-methylphenyl | CH₃ | H | Cl | 2 | cis | |
| I.379 | C₂H₅ | CH₃ | 4-methylphenyl | CH₃ | H | Cl | 2 | cis | |
| I.380 | C₂H₅ | CH₃ | 4-chlorophenyl | CH₃ | H | Cl | 2 | cis | |

TABLE 1-continued

[Structure: pyrazolone with R¹-N, R⁷, =X substituent, and phenyl ring bearing R², R³, and O_nS-R⁴ groups]

| No. | R¹ | R² | R³ | R⁴ | R⁷ | X | n | Isomer | Phys. Data |
|---|---|---|---|---|---|---|---|---|---|
| I.381 | C₂H₅ | CH₃ | 2-chlorophenyl | CH₃ | H | Cl | 2 | cis | |
| I.382 | C₂H₅ | CH₃ | 3-chlorophenyl | CH₃ | H | Cl | 2 | cis | |
| I.383 | C₂H₅ | CH₃ | 4-methoxyphenyl | CH₃ | H | Cl | 2 | cis | |
| I.384 | C₂H₅ | CH₃ | methylthio | CH₃ | H | Cl | 2 | cis | |
| I.385 | C₂H₅ | CH₃ | methoxy | CH₃ | H | Cl | 2 | cis | |
| I.386 | C₂H₅ | CH₃ | ethoxy | CH₃ | H | Cl | 2 | cis | |
| I.387 | C₂H₅ | CH₃ | 2-methoxyethoxy | CH₃ | H | Cl | 2 | cis | |
| I.388 | C₂H₅ | CH₃ | formyl | CH₃ | H | Cl | 2 | cis | |
| I.389 | C₂H₅ | CH₃ | acetylamino | CH₃ | H | Cl | 2 | cis | |
| I.390 | C₂H₅ | CH₃ | methylcarbonyl | CH₃ | H | Cl | 2 | cis | |
| I.391 | C₂H₅ | CH₃ | methoxycarbonyl | CH₃ | H | Cl | 2 | cis | |
| I.392 | C₂H₅ | CH₃ | dimethylaminocarbonyl | CH₃ | H | Cl | 2 | cis | |
| I.393 | C₂H₅ | CH₃ | methoxyiminomethyl | CH₃ | H | Cl | 2 | cis | |
| I.394 | C₂H₅ | CH₃ | ethoxyiminomethyl | CH₃ | H | Cl | 2 | cis | |
| I.395 | C₂H₅ | CH₃ | 1-ethoxyiminoethyl | CH₃ | H | Cl | 2 | cis | |
| I.396 | C₂H₅ | CH₃ | 1-methoxyiminoethyl | CH₃ | H | Cl | 2 | cis | |
| I.397 | C₂H₅ | CH₃ | 1-ethoxyiminopropyl | CH₃ | H | Cl | 2 | cis | |
| I.398 | C₂H₅ | CH₃ | 1-methoxyiminopropyl | CH₃ | H | Cl | 2 | cis | |
| I.399 | C₂H₅ | CH₃ | cyano | CH₃ | H | Cl | 2 | cis | |
| I.400 | CH₃ | Cl | H | CF₃ | H | Cl | 2 | cis | |
| I.401 | CH₃ | Cl | F | CF₃ | H | Cl | 2 | cis | |
| I.402 | CH₃ | Cl | Cl | CF₃ | H | Cl | 2 | cis | |
| I.403 | CH₃ | Cl | Br | CF₃ | H | Cl | 2 | cis | |
| I.404 | CH₃ | Cl | CH₃ | CF₃ | H | Cl | 2 | cis | |
| I.405 | CH₃ | Cl | CF₃ | CF₃ | H | Cl | 2 | cis | |
| I.406 | CH₃ | Cl | ethyl | CF₃ | H | Cl | 2 | cis | |
| I.407 | CH₃ | Cl | trans-chloroallyl | CF₃ | H | Cl | 2 | cis | |
| I.408 | CH₃ | Cl | 2,2-dichlorovinyl | CF₃ | H | Cl | 2 | cis | |
| I.409 | CH₃ | Cl | 4,5-dihydroisoxazol-3-yl | CF₃ | H | Cl | 2 | cis | |
| I.410 | CH₃ | Cl | isoxazol-3-yl | CF₃ | H | Cl | 2 | cis | |
| I.411 | CH₃ | Cl | 3-methylisoxazol-5-yl | CF₃ | H | Cl | 2 | cis | |
| I.412 | CH₃ | Cl | 4-methyl-4,5-dihydroisoxazol-3-yl | CF₃ | H | Cl | 2 | cis | |
| I.413 | CH₃ | Cl | 5-methyl-4,5-dihydroisoxazol-3-yl | CF₃ | H | Cl | 2 | cis | |
| I.414 | CH₃ | Cl | thiazol-2-yl | CF₃ | H | Cl | 2 | cis | |
| I.415 | CH₃ | Cl | oxazol-2-yl | CF₃ | H | Cl | 2 | cis | |
| I.416 | CH₃ | Cl | 4,5-dihydrooxazol-2-yl | CF₃ | H | Cl | 2 | cis | |
| I.417 | CH₃ | Cl | 1-methylpyrazol-3-yl | CF₃ | H | Cl | 2 | cis | |
| I.418 | CH₃ | Cl | 2-thienyl | CF₃ | H | Cl | 2 | cis | |
| I.419 | CH₃ | Cl | 3-thienyl | CF₃ | H | Cl | 2 | cis | |
| I.420 | CH₃ | Cl | [1,3]dioxolan-2-yl | CF₃ | H | Cl | 2 | cis | |
| I.421 | CH₃ | Cl | 2-pyridyl | CF₃ | H | Cl | 2 | cis | |
| I.422 | CH₃ | Cl | 3-pyridyl | CF₃ | H | Cl | 2 | cis | |
| I.423 | CH₃ | Cl | 4-pyridyl | CF₃ | H | Cl | 2 | cis | |
| I.424 | CH₃ | Cl | pyrimidin-2-yl | CF₃ | H | Cl | 2 | cis | |
| I.425 | CH₃ | Cl | pyrimidin-4-yl | CF₃ | H | Cl | 2 | cis | |
| I.426 | CH₃ | Cl | pyrazin-2-yl | CF₃ | H | Cl | 2 | cis | |
| I.427 | CH₃ | Cl | pyridazin-3-yl | CF₃ | H | Cl | 2 | cis | |
| I.428 | CH₃ | Cl | phenyl | CF₃ | H | Cl | 2 | cis | |
| I.429 | CH₃ | Cl | 2-fluorophenyl | CF₃ | H | Cl | 2 | cis | |
| I.430 | CH₃ | Cl | 3-trifluoromethylphenyl | CF₃ | H | Cl | 2 | cis | |
| I.431 | CH₃ | Cl | 4-methylphenyl | CF₃ | H | Cl | 2 | cis | |
| I.432 | CH₃ | Cl | 4-chlorophenyl | CF₃ | H | Cl | 2 | cis | |
| I.433 | CH₃ | Cl | 4-methoxyphenyl | CF₃ | H | Cl | 2 | cis | |
| I.434 | CH₃ | Cl | methoxy | CF₃ | H | Cl | 2 | cis | |
| I.435 | CH₃ | Cl | dimethylaminocarbonyl | CF₃ | H | Cl | 2 | cis | |
| I.436 | CH₃ | Cl | methoxyiminomethyl | CF₃ | H | Cl | 2 | cis | |
| I.437 | CH₃ | Cl | H | CH₃ | H | Cl | 1 | cis | |
| I.438 | CH₃ | Cl | Cl | CH₃ | H | Cl | 1 | cis | |
| I.439 | CH₃ | Cl | CH₃ | CH₃ | H | Cl | 1 | cis | |
| I.440 | CH₃ | Cl | 4,5-dihydroisoxazol-3-yl | CH₃ | H | Cl | 1 | cis | |
| I.441 | CH₃ | Cl | isoxazol-3-yl | CH₃ | H | Cl | 1 | cis | |

TABLE 1-continued

![Chemical structure showing pyrazolone with R1-N, R7, X substituents and phenyl ring with R2, R3, and OnS-R4 groups]

| No. | R¹ | R² | R³ | R⁴ | R⁷ | X | n | Isomer | Phys. Data |
|---|---|---|---|---|---|---|---|---|---|
| I.442 | CH₃ | Cl | 3-methylisoxazol-5-yl | CH₃ | H | Cl | 1 | cis | |
| I.443 | CH₃ | Cl | thiazol-2-yl | CH₃ | H | Cl | 1 | cis | |
| I.444 | CH₃ | Cl | oxazol-2-yl | CH₃ | H | Cl | 1 | cis | |
| I.445 | CH₃ | Cl | 2-pyridyl | CH₃ | H | Cl | 1 | cis | |
| I.446 | CH₃ | Cl | pyrimidin-2-yl | CH₃ | H | Cl | 1 | cis | |
| I.447 | CH₃ | Cl | pyrazin-2-yl | CH₃ | H | Cl | 1 | cis | |
| I.448 | CH₃ | Cl | phenyl | CH₃ | H | Cl | 1 | cis | |
| I.449 | CH₃ | Cl | methoxy | CH₃ | H | Cl | 1 | cis | |
| I.450 | CH₃ | Cl | H | CH₃ | H | Cl | 0 | cis | |
| I.451 | CH₃ | Cl | Cl | CH₃ | H | Cl | 0 | cis | |
| I.452 | CH₃ | Cl | CH₃ | CH₃ | H | Cl | 0 | cis | |
| I.453 | CH₃ | Cl | 4,5-dihydroisoxazol-3-yl | CH₃ | H | Cl | 0 | cis | |
| I.454 | CH₃ | Cl | isoxazol-3-yl | CH₃ | H | Cl | 0 | cis | |
| I.455 | CH₃ | Cl | 3-methylisoxazol-5-yl | CH₃ | H | Cl | 0 | cis | |
| I.456 | CH₃ | Cl | thiazol-2-yl | CH₃ | H | Cl | 0 | cis | |
| I.457 | CH₃ | Cl | oxazol-2-yl | CH₃ | H | Cl | 0 | cis | |
| I.458 | CH₃ | Cl | 2-pyridyl | CH₃ | H | Cl | 0 | cis | |
| I.459 | CH₃ | Cl | pyrimidin-2-yl | CH₃ | H | Cl | 0 | cis | |
| I.460 | CH₃ | Cl | pyrazin-2-yl | CH₃ | H | Cl | 0 | cis | |
| I.461 | CH₃ | Cl | phenyl | CH₃ | H | Cl | 0 | cis | |
| I.462 | CH₃ | Cl | methoxy | CH₃ | H | Cl | 0 | cis | |
| I.463 | CH₃ | Cl | H | CH₃ | H | Br | 2 | cis | |
| I.464 | CH₃ | Cl | Cl | CH₃ | H | Br | 2 | cis | |
| I.465 | CH₃ | Cl | CH₃ | CH₃ | H | Br | 2 | cis | |
| I.466 | CH₃ | Cl | 4,5-dihydroisoxazol-3-yl | CH₃ | H | Br | 2 | cis | see Example 3 |
| I.467 | CH₃ | Cl | isoxazol-3-yl | CH₃ | H | Br | 2 | cis | |
| I.468 | CH₃ | Cl | 3-methylisoxazol-5-yl | CH₃ | H | Br | 2 | cis | |
| I.469 | CH₃ | Cl | thiazol-2-yl | CH₃ | H | Br | 2 | cis | |
| I.470 | CH₃ | Cl | oxazol-2-yl | CH₃ | H | Br | 2 | cis | |
| I.471 | CH₃ | Cl | 2-pyridyl | CH₃ | H | Br | 2 | cis | |
| I.472 | CH₃ | Cl | pyrimidin-2-yl | CH₃ | H | Br | 2 | cis | |
| I.473 | CH₃ | Cl | pyrazin-2-yl | CH₃ | H | Br | 2 | cis | |
| I.474 | CH₃ | Cl | phenyl | CH₃ | H | Br | 2 | cis | |
| I.475 | CH₃ | Cl | methoxy | CH₃ | H | Br | 2 | cis | |
| I.476 | CH₃ | Cl | H | CH₃ | H | H | 2 | cis | |
| I.477 | CH₃ | Cl | Cl | CH₃ | H | H | 2 | cis | |
| I.478 | CH₃ | Cl | CH₃ | CH₃ | H | H | 2 | cis | |
| I.479 | CH₃ | Cl | 4,5-dihydroisoxazol-3-yl | CH₃ | H | H | 2 | cis | |
| I.480 | CH₃ | Cl | isoxazol-3-yl | CH₃ | H | H | 2 | cis | |
| I.481 | CH₃ | Cl | 3-methylisoxazol-5-yl | CH₃ | H | H | 2 | cis | |
| I.482 | CH₃ | Cl | thiazol-2-yl | CH₃ | H | H | 2 | cis | |
| I.483 | CH₃ | Cl | oxazol-2-yl | CH₃ | H | H | 2 | cis | |
| I.484 | CH₃ | Cl | 2-pyridyl | CH₃ | H | H | 2 | cis | |
| I.485 | CH₃ | Cl | pyrimidin-2-yl | CH₃ | H | H | 2 | cis | |
| I.486 | CH₃ | Cl | pyrazin-2-yl | CH₃ | H | H | 2 | cis | |
| I.487 | CH₃ | Cl | phenyl | CH₃ | H | H | 2 | cis | |
| I.488 | CH₃ | Cl | methoxy | CH₃ | H | H | 2 | cis | |
| I.489 | CH₃ | Cl | H | CH₃ | H | Cl | 2 | trans | |
| I.490 | CH₃ | Cl | Cl | CH₃ | H | Cl | 2 | trans | |
| I.491 | CH₃ | Cl | CH₃ | CH₃ | H | Cl | 2 | trans | |
| I.492 | CH₃ | Cl | 4,5-dihydroisoxazol-3-yl | CH₃ | H | Cl | 2 | trans | |
| I.493 | CH₃ | Cl | isoxazol-3-yl | CH₃ | H | Cl | 2 | trans | |
| I.494 | CH₃ | Cl | 3-methylisoxazol-5-yl | CH₃ | H | Cl | 2 | trans | |
| I.495 | CH₃ | Cl | thiazol-2-yl | CH₃ | H | Cl | 2 | trans | |
| I.496 | CH₃ | Cl | oxazol-2-yl | CH₃ | H | Cl | 2 | trans | |
| I.497 | CH₃ | Cl | 2-pyridyl | CH₃ | H | Cl | 2 | trans | |
| I.498 | CH₃ | Cl | pyrimidin-2-yl | CH₃ | H | Cl | 2 | trans | |
| I.499 | CH₃ | Cl | pyrazin-2-yl | CH₃ | H | Cl | 2 | trans | |
| I.500 | CH₃ | Cl | phenyl | CH₃ | H | Cl | 2 | trans | |
| I.501 | CH₃ | Cl | methoxy | CH₃ | H | Cl | 2 | trans | |
| I.502 | CH₃ | Cl | H | CH₃ | CH₃ | Cl | 2 | cis | |

TABLE 1-continued

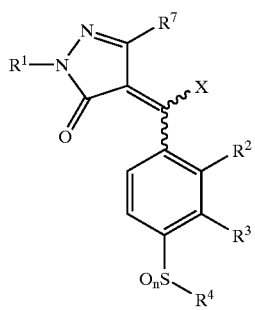

| No. | R¹ | R² | R³ | R⁴ | R⁷ | X | n | Isomer | Phys. Data |
|---|---|---|---|---|---|---|---|---|---|
| I.503 | CH₃ | Cl | Cl | CH₃ | CH₃ | Cl | 2 | cis | |
| I.504 | CH₃ | Cl | CH₃ | CH₃ | CH₃ | Cl | 2 | cis | |
| I.505 | CH₃ | Cl | 4,5-dihydroisoxazol-3-yl | CH₃ | CH₃ | Cl | 2 | cis | |
| I.506 | CH₃ | Cl | isoxazol-3-yl | CH₃ | CH₃ | Cl | 2 | cis | |
| I.507 | CH₃ | Cl | 3-methylisoxazol-5-yl | CH₃ | CH₃ | Cl | 2 | cis | |
| I.508 | CH₃ | Cl | thiazol-2-yl | CH₃ | CH₃ | Cl | 2 | cis | |
| I.509 | CH₃ | Cl | oxazol-2-yl | CH₃ | CH₃ | Cl | 2 | cis | |
| I.510 | CH₃ | Cl | 2-pyridyl | CH₃ | CH₃ | Cl | 2 | cis | |
| I.511 | CH₃ | Cl | pyrimidin-2-yl | CH₃ | CH₃ | Cl | 2 | cis | |
| I.512 | CH₃ | Cl | pyrazin-2-yl | CH₃ | CH₃ | Cl | 2 | cis | |
| I.513 | CH₃ | Cl | phenyl | CH₃ | CH₃ | Cl | 2 | cis | |
| I.514 | CH₃ | Cl | methoxy | CH₃ | CH₃ | Cl | 2 | cis | |

TABLE 2

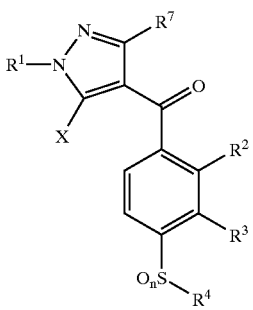

| No. | R¹ | R² | R³ | R⁴ | R⁷ | X | n | Phys. Data |
|---|---|---|---|---|---|---|---|---|
| II.1 | CH₃ | Cl | H | CH₃ | H | Br | 2 | |
| II.2 | CH₃ | Cl | Cl | CH₃ | H | Br | 2 | |
| II.3 | CH₃ | Cl | CH₃ | CH₃ | H | Br | 2 | |
| II.4 | CH₃ | Cl | 4,5-dihydroisoxazol-3-yl | CH₃ | H | Br | 2 | |
| II.5 | CH₃ | Cl | isoxazol-3-yl | CH₃ | H | Br | 2 | |
| II.6 | CH₃ | Cl | 3-methylisoxazol-5-yl | CH₃ | H | Br | 2 | |
| II.7 | CH₃ | Cl | thiazol-2-yl | CH₃ | H | Br | 2 | |
| II.8 | CH₃ | Cl | oxazol-2-yl | CH₃ | B | Br | 2 | |
| II.9 | CH₃ | Cl | 2-pyridyl | CH₃ | H | Br | 2 | |
| II.10 | CH₃ | Cl | pyrimidin-2-yl | CH₃ | H | Br | 2 | |
| II.11 | CH₃ | Cl | pyrazin-2-yl | CH₃ | H | Br | 2 | |
| II.12 | CH₃ | Cl | phenyl | CH₃ | H | Br | 2 | |
| II.13 | CH₃ | Cl | methoxy | CH₃ | H | Br | 2 | |
| II.14 | CH₃ | Cl | H | CH₃ | H | Cl | 2 | |
| II.15 | CH₃ | Cl | Cl | CH₃ | H | Cl | 2 | |
| II.16 | CH₃ | Cl | CH₃ | CH₃ | H | Cl | 2 | |
| II.17 | CH₃ | Cl | 4,5-dihydroisoxazol-3-yl | CH₃ | H | Cl | 2 | see Example 1 |
| II.18 | CH₃ | Cl | isoxazol-3-yl | CH₃ | H | Cl | 2 | |
| II.19 | CH₃ | Cl | 3-methylisoxazol-5-yl | CH₃ | H | Cl | 2 | |
| II.20 | CH₃ | Cl | thiazol-2-yl | CH₃ | H | Cl | 2 | ¹H NMR (270 MHz, CDCl₃); 8.18 (d, 1H); 7.99 (d, 1H); 7.78 (d, 1H); 7.62 (m, 2H); 3.22 (s, 3H); 1.62 (s, 3H) |

TABLE 2-continued

| No. | R¹ | R² | R³ | R⁴ | R⁷ | X | n | Phys. Data |
|---|---|---|---|---|---|---|---|---|
| II.21 | CH₃ | Cl | oxazol-2-yl | CH₃ | H | Cl | 2 | |
| II.22 | CH₃ | Cl | 2-pyridyl | CH₃ | H | Cl | 2 | |
| II.23 | CH₃ | Cl | pyrimidin-2-yl | CH₃ | H | Cl | 2 | |
| II.24 | CH₃ | Cl | pyrazin-2-yl | CH₃ | H | Cl | 2 | |
| II.25 | CH₃ | Cl | phenyl | CH₃ | H | Cl | 2 | |
| II.26 | CH₃ | Cl | methoxy | CH₃ | H | Cl | 2 | |
| II.27 | CH₃ | CH₃ | H | CH₃ | H | Cl | 2 | |
| II.28 | CH₃ | CH₃ | Cl | CH₃ | H | Cl | 2 | |
| II.29 | CH₃ | CH₃ | CH₃ | CH₃ | H | Cl | 2 | |
| II.30 | CH₃ | CH₃ | 4,5-dihydroisoxazol-3-yl | CH₃ | H | Cl | 2 | |
| II.31 | CH₃ | CH₃ | isoxazol-3-yl | CH₃ | H | Cl | 2 | |
| II.32 | CH₃ | CH₃ | 3-methylisoxazol-5-yl | CH₃ | H | Cl | 2 | |
| II.33 | CH₃ | CH₃ | thiazol-2-yl | CH₃ | H | Cl | 2 | |
| II.34 | CH₃ | CH₃ | oxazol-2-yl | CH₃ | H | Cl | 2 | |
| II.35 | CH₃ | CH₃ | 2-pyridyl | CH₃ | H | Cl | 2 | |
| II.36 | CH₃ | CH₃ | pyrimidin-2-yl | CH₃ | H | Cl | 2 | |
| II.37 | CH₃ | CH₃ | pyrazin-2-yl | CH₃ | H | Cl | 2 | |
| II.38 | CH₃ | CH₃ | phenyl | CH₃ | H | Cl | 2 | |
| II.39 | CH₃ | CH₃ | methoxy | CH₃ | H | Cl | 2 | |
| II.40 | CH₃CH₂ | Cl | H | CH₃ | H | Br | 2 | |
| II.41 | CH₃CH₂ | Cl | Cl | CH₃ | H | Br | 2 | |
| II.42 | CH₃CH₂ | Cl | CH₃ | CH₃ | H | Br | 2 | |
| II.43 | CH₃CH₂ | Cl | 4,5-dihydroisoxazol-3-yl | CH₃ | H | Br | 2 | |
| II.44 | CH₃CH₂ | Cl | isoxazol-3-yl | CH₃ | H | Br | 2 | |
| II.45 | CH₃CH₂ | Cl | 3-methylisoxazol-5-yl | CH₃ | H | Br | 2 | |
| II.46 | CH₃CH₂ | Cl | thiazol-2-yl | CH₃ | H | Br | 2 | |
| II.47 | CH₃CH₂ | Cl | oxazol-2-yl | CH₃ | H | Br | 2 | |
| II.48 | CH₃CH₂ | Cl | 2-pyridyl | CH₃ | H | Br | 2 | |
| II.49 | CH₃CH₂ | Cl | pyrimidin-2-yl | CH₃ | H | Br | 2 | |
| II.50 | CH₃CH₂ | Cl | pyrazin-2-yl | CH₃ | H | Br | 2 | |
| II.51 | CH₃CH₂ | Cl | phenyl | CH₃ | H | Br | 2 | |
| II.52 | CH₃CH₂ | Cl | methoxy | CH₃ | H | Br | 2 | |
| II.53 | CH₃CH₂ | Cl | H | CH₃ | H | Cl | 2 | |
| II.54 | CH₃CH₂ | Cl | Cl | CH₃ | H | Cl | 2 | |
| II.55 | CH₃CH₂ | Cl | CH₃ | CH₃ | H | Cl | 2 | |
| II.56 | CH₃CH₂ | Cl | 4,5-dihydroisoxazol-3-yl | CH₃ | H | Cl | 2 | |
| II.57 | CH₃CH₂ | Cl | isoxazol-3-yl | CH₃ | H | Cl | 2 | |
| II.58 | CH₃CH₂ | Cl | 3-methylisoxazol-5-yl | CH₃ | H | Cl | 2 | |
| II.59 | CH₃CH₂ | Cl | thiazol-2-yl | CH₃ | H | Cl | 2 | ¹H NMR (270 MHz, CDCl₃); 8.28 (d, 1H); 7.99 (d, 1H); 7.75 (s, 1H); 7.68 (d, 1H); 4.28 (q, 2H); 3.29 (s, 3H); 1.45 (t, 3H) |
| II.60 | CH₃CH₂ | Cl | oxazol-2-yl | CH₃ | H | Cl | 2 | |
| II.61 | CH₃CH₂ | Cl | 2-pyridyl | CH₃ | H | Cl | 2 | |
| II.62 | CH₃CH₂ | Cl | pyrimidin-2-yl | CH₃ | H | Cl | 2 | |
| II.63 | CH₃CH₂ | Cl | pyrazin-2-yl | CH₃ | H | Cl | 2 | |
| II.64 | CH₃CH₂ | Cl | phenyl | CH₃ | H | Cl | 2 | |
| II.65 | CH₃CH₂ | Cl | methoxy | CH₃ | H | Cl | 2 | |
| II.66 | CH₃CH₂ | CH₃ | H | CH₃ | H | Cl | 2 | |
| II.67 | CH₃CH₂ | CH₃ | Cl | CH₃ | H | Cl | 2 | |
| II.68 | CH₃CH₂ | CH₃ | CH₃ | CH₃ | H | Cl | 2 | |
| II.69 | CH₃CH₂ | CH₃ | 4,5-dihydroisoxazol-3-yl | CH₃ | H | Cl | 2 | |
| II.70 | CH₃CH₂ | CH₃ | isoxazol-3-yl | CH₃ | H | Cl | 2 | |
| II.71 | CH₃CH₂ | CH₃ | 3-methylisoxazol-5-yl | CH₃ | H | Cl | 2 | |
| II.72 | CH₃CH₂ | CH₃ | thiazol-2-yl | CH₃ | H | Cl | 2 | |
| II.73 | CH₃CH₂ | CH₃ | oxazol-2-yl | CH₃ | H | Cl | 2 | |

TABLE 2-continued

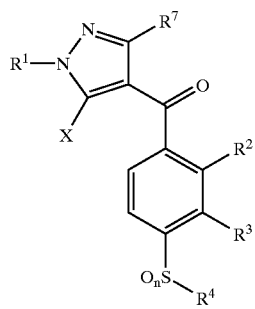

| No. | $R^1$ | $R^2$ | $R^3$ | $R^4$ | $R^7$ | X | n | Phys. Data |
|---|---|---|---|---|---|---|---|---|
| II.74 | CH$_3$CH$_2$ | CH$_3$ | 2-pyridyl | CH$_3$ | H | Cl | 2 | |
| II.75 | CH$_3$CH$_2$ | CH$_3$ | pyrimidin-2-yl | CH$_3$ | H | Cl | 2 | |
| II.76 | CH$_3$CH$_2$ | CH$_3$ | pyrazin-2-yl | CH$_3$ | H | Cl | 2 | |
| II.77 | CH$_3$CH$_2$ | CH$_3$ | phenyl | CH$_3$ | H | Cl | 2 | |
| II.78 | CH$_3$CH$_2$ | CH$_3$ | methoxy | CH$_3$ | H | Cl | 2 | |

The compounds I and their agriculturally useful salts are suitable, both in the form of isomer mixtures and in the form of the pure isomers, as herbicides. The herbicidal compositions comprising I control vegetation on non-crop areas very efficiently, especially at high rates of application. They act against broad-leaved weeds and grass weeds in crops such as wheat, rice, maize, soya and cotton without causing any significant damage to the crop plants. This effect is mainly observed at low rates of application.

Depending on the application method in question, the compounds of the formula I, or compositions comprising them, can additionally be employed in a further number of crop plants for eliminating undesirable plants. Examples of suitable crops are the following:

*Allium cepa, Ananas comosus, Arachis hypogaea, Asparagus officinalis, Beta vulgaris* spec. *altissima, Beta vulgaris* spec. *rapa, Brassica napus* var. *napus, Brassica napus* var. *napobrassica, Brassica rapa* var. *silvestris, Camellia sinensis, Carthamus tinctorius, Carya illinoinensis, Citrus limon, Citrus sinensis, Coffea arabica (Coffea canephora, Coffea liberica), Cucumis sativus, Cynodon dactylon, Daucus carota, Elaeis guineensis, Fragaria vesca, Glycine max, Gossypium hirsutum, (Gossypium arboreum, Gossypium herbaceum, Gossypium vitifolium), Helianthus annuus, Hevea brasiliensis, Hordeum vulgare, Humulus lupulus, Ipomoea batatas, Juglans regia, Lens culinaris, Linum usitatissimum, Lycopersicon lycopersicum,* Malus spec., *Manihot esculenta, Medicago sativa,* Musa spec., *Nicotiana tabacum (N.rustica), Olea europaea, Oryza sativa, Phaseolus lunatus, Phaseolus vulgaris, Picea abies,* Pinus spec., *Pisum sativum, Prunus avium, Prunus persica, Pyrus communis, Ribes sylvestre, Ricinus communis, Saccharum officinarum, Secale cereale, Solanum tuberosum, Sorghum bicolor (s. vulgare), Theobroma cacao, Trifolium pratense, Triticum aestivum, Triticum durum, Vicia faba, Vitis vinifera* and *Zea mays.*

In addition, the compounds I may also be used in crops which tolerate the action of herbicides owing to breeding, including genetic engineering methods.

The active compounds or the herbicidal compositions can be applied pre- or post-emergence. If the active compounds are less well tolerated by certain crop plants, application techniques may be used in which the herbicidal compositions are sprayed, with the aid of the spraying equipment, in such a way that they come into as little contact as possible, if any, with the leaves of the sensitive crop plants, while the active compounds reach the leaves of undesirable plants growing underneath, or the bare soil surface (post-directed, lay-by).

The compounds I, or the herbicidal compositions comprising them, can be used for example in the form of ready-to-spray aqueous solutions, powders, suspensions, also highly-concentrated aqueous, oily or other suspensions or dispersions, emulsions, oil dispersions, pastes, dusts, materials for spreading, or granules, by means of spraying, atomizing, dusting, spreading or watering. The use forms depend on the intended use; in any case, they should guarantee the finest possible distribution of the active compounds according to the invention.

Suitable inert auxiliaries are essentially: mineral oil fractions of medium to high boiling point, such as kerosene and diesel oil, furthermore coal tar oils and oils of vegetable or animal origin, aliphatic, cyclic and aromatic hydrocarbons, e.g. paraffin, tetrahydronaphthalene, alkylated naphthalenes and their derivatives, alkylated benzenes and their derivatives, alcohols such as methanol, ethanol, propanol, butanol and cyclohexanol, ketones such as cyclohexanone, strongly polar solvents, e.g. amines such as N-methylpyrrolidone, and water.

Aqueous use forms can be prepared from emulsion concentrates, suspensions, pastes, wettable powders or water-dispersible granules by adding water. To prepare emulsions, pastes or oil dispersions, the benzylidenepyrazolones, either as such or dissolved in an oil or solvent, can be homogenized in water by means of a wetting agent, tackifier, dispersant or emulsifier. Alternatively, it is possible to prepare concentrates comprising active compound, wetting agent, tackifier, dispersant or emulsifier and, if desired, solvent or oil, which are suitable for dilution with water.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl sulfates, lauryl ether sulfates and fatty alcohol sulfates, and salts of sulfated hexa-, hepta- and octadecanols, and also of fatty alcohol glycol ether, condensates of sulfonated naphthalene and its derivatives with formaldehyde, condensates of naphthalene, or of the naphthalenesulfonic acids with phenol and formaldehyde, polyoxyethylene octylphenol ether, ethoxylated isooctyl-, octyl- or nonylphenol, alkylphenyl or tributylphenyl polyglycol ether, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignin-sulfite waste liquors or methylcellulose.

Powders, materials for scattering and dusts can be prepared by mixing or grinding the active compounds together with a solid carrier.

Granules, e.g. coated granules, impregnated granules and homogeneous granules, can be prepared by binding the active ingredients to solid carriers. Solid carriers are mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials, fertilizers such as ammonium sulfate, ammonium phosphate and ammonium nitrate, ureas, and products of vegetable origin, such as cereal meal, tree bark meal, wood meal and nutshell meal, cellulose powders, or other solid carriers.

The concentrations of the active compounds I in the ready-to-use preparations can be varied within wide ranges. In general, the formulations comprise from 0.001 to 98% by weight, preferably 0.01 to 95% by weight of at least one active compound. The active compounds are employed in a purity of from 90% to 100%, preferably 95% to 100% (according to NMR spectrum).

The formulation examples which follow illustrate the preparation of the compounds I according to the invention:

I. 20 parts by weight of the compound No. I.20 are dissolved in a mixture composed of 80 parts by weight of alkylated benzene, 10 parts by weight of the adduct of 8 to 10 mol of ethylene oxide to 1 mol of oleic acid N-monoethanolamide, 5 parts by weight of calcium dodecylbenzenesulfonate and 5 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

II. 20 parts by weight of the compound No. I.119 are dissolved in a mixture composed of 40 parts by weight of cyclohexanone, 30 parts by weight of isobutanol, 20 parts by weight of the adduct of 7 mol of ethylene oxide to 1 mol of isooctylphenol and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

III. 20 parts by weight of the active compound No. I.466 are dissolved in a mixture composed of 25 parts by weight of cyclohexanone, 65 parts by weight of a mineral oil fraction of boiling point 210 to 280° C. and 10 parts by weight of the adduct of 40 mol of ethylene oxide to 1 mol of castor oil. Pouring the solution into 100,000 parts by weight of water and finely distributing it therein gives an aqueous dispersion which comprises 0.02% by weight of the active compound.

IV. 20 parts by weight of the active compound No. I.20 are mixed thoroughly with 3 parts by weight of the sodium salt of diisobutylnaphthalenesulfonate, 17 parts by weight of the sodium salt of a lignosulfonic acid from a sulfite waste liquor and 60 parts by weight of pulverulent silica gel, and the mixture is ground in a hammer mill. Finely distributing the mixture in 20,000 parts by weight of water gives a spray mixture which comprises 0.1% by weight of the active compound.

V. 3 parts by weight of the active compound No. I.119 are mixed with 97 parts by weight of finely divided kaolin. This gives a dust which comprises 3% by weight of active compound.

VI. 20 parts by weight of the active compound No. I.466 are mixed intimately with 2 parts by weight of the calcium salt of the dodecylbenzenesulfonate, 8 parts by weight of fatty alcohol polyglycol ether, 2 parts by weight of the sodium salt of a phenol/urea/formaldehyde condensate and 68 parts by weight of a paraffinic mineral oil. This gives a stable oily dispersion.

VII. 1 part by weight of the compound No. I.20 is dissolved in a mixture composed of 70 parts by weight of cyclo-hexanone, 20 parts by weight of ethoxylated iso-octylphenol and 10 parts by weight of ethoxylated castor oil. This gives a stable emulsion concentrate.

VIII. 1 part by weight of the compound No. I.119 is dissolved in a mixture composed of 80 parts by weight of cyclohexanone and 20 parts by weight of Wettol OR [sic] EM 31 (nonionic emulsifier based on ethoxylated castor oil). This gives a stable emulsion concentrate.

To widen the spectrum of action and to achieve synergistic effects, the benzylidenepyrazolones may be mixed with a large number of representatives of other herbicidal or growth-regulating active compound groups and then applied concomitantly. Suitable components for mixtures are, for example, 1,2,4-thiadiazoles, 1,3,4-thiadiazoles, amides, aminophosphoric acid and its derivatives, aminotriazoles, anilides, (het)aryloxyalkanoic acid and its derivatives, benzoic acid and its derivatives, benzothiadiazinones, 2-aroyl-1,3-cyclohexanediones, hetaryl aryl ketones, benzylisoxazolidinones, meta-$CF_3$-phenyl derivatives, carbamates, quinolinecarboxylic acid and its derivates, chloroacetanilides, cyclohexane-1,3-dione derivatives, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, 3-phenyluracils, imidazoles, imidazolinones, N-phenyl-3,4,5,6-tetrahydrophthalimides, oxadiazoles, oxiranes, phenols, aryloxy- and hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides and uracils.

It may furthermore be advantageous to apply the compounds I, alone or in combination with other herbicides, in the form of a mixture with other crop protection agents, for example together with agents for controlling pests or phytopathogenic fungi or bacteria. Also of interest is the miscibility with mineral salt solutions, which are employed for treating nutritional and trace element deficiencies. Non-phytotoxic oils and oil concentrates may also be added.

The rates of application of active compound are from 0.001 to 3.0, preferably 0.01 to 1.0, kg/ha of active substance (a.s.), depending on the control target, the season, the target plants and the growth stage.

USE EXAMPLES

The herbicidal activity of the benzylidenepyrazolones of the formula I was demonstrated by the following greenhouse experiments:

The culture containers used were plastic pots containing loamy sand with approximately 3.0% of humus as the substrate. The seeds of the test plants were sown separately for each species.

For the pre-emergence treatment, the active compounds, which had been suspended or emulsified in water, were applied directly after sowing by means of finely distributing nozzles. The containers were irrigated gently to promote germination and growth and subsequently covered with translucent plastic hoods until the plants had rooted. This cover caused uniform germination of the test plants, unless this was adversely affected by the active compounds.

For the post-emergence treatment, the test plants were first grown to a plant height of 3 to 15 cm, depending on the plant habit, and only then treated with the active compounds which had been suspended or emulsified in water. The test plants for this purpose were either sown directly and grown in the same containers, or they were first grown separately as seedlings and transplanted into the test containers a few days prior to treatment. The rate of application for the post-emergence treatment was 0.125 or 0.0≅kg/ha of a.s.

Depending on the species, the plants were kept at 10–25° C. or 20–35° C. The test period extended over 2 to 4 weeks. During this time, the plants were tended, and their response to the individual treatments was evaluated.

Evaluation was carried out using a scale from 0 to 100. 100 means no emergence of the plants, or complete destruction of at least the aerial parts, and 0 means no damage, or normal course of growth.

The plants used in the greenhouse experiments were from the following species:

| Scientific name | Common name |
| --- | --- |
| Harmful plants | |
| Chenopodium album | lambsquarters |
| Echinochloa crus-galli | barnyard grass |
| Polygonum persicaria | ladys thumb |
| Setaria faberii | giant foxtail |
| Useful plant | |
| Zea mays | corn |

The result showed that compound No. I.119 controls the abovementioned harmful plants very effectively (>98% damage of the plants), while the useful plant maize was not noticeably damaged (0% damage) by the treatment.

The comparative experiment stated in Table A shows the improved herbicidal action of the compound I.119 according to the invention compared to the compound A, known from JP-A 61268670 (CA, 106 : 209479).

TABLE A

Post-emergence greenhouse experiments

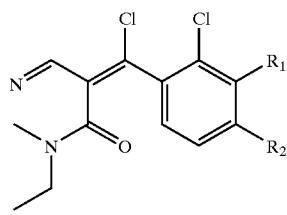

| Ex. No. | I.119 | A |
| --- | --- | --- |
| $R_1$ | 4,5-dihydroisox-azol-3-yl | H |

TABLE A-continued

Post-emergence greenhouse experiments

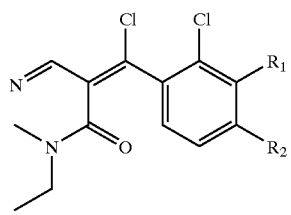

| Ex. No. | I.119 | | A | |
| --- | --- | --- | --- | --- |
| $R_2$ | $SO_2CH_3$ | | Cl | |
| Application rate (g/ha of a.s.) | 0.5 | 0.25 | 0.5 | 0.25 |
| Test plants [damage in %] | | | | |
| Amaranthus retroflexus | 100 | 100 | 40 | 30 |
| Echinochloa crus-galli | 100 | 100 | 80 | 70 |
| Setaria faberii | 100 | 100 | 10 | 10 |
| Solanum nigrum | 100 | 100 | 70 | 50 |

We claim:
1. A benzoylpyrazole of formula II

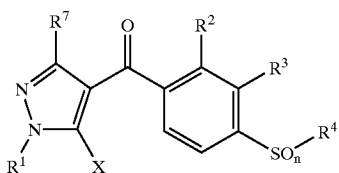

wherein
R$^1$ is C$_1$–C$_4$-alkyl or C$_1$–C$_4$-haloalkyl;
R$^2$ is C$_1$–C$_4$-alkyl, C$_1$–C$_4$-haloalkyl, C$_1$–C$_4$-alkoxy, C$_1$–C$_4$-haloalkoxy or halogen;
R$^3$ is an unsubstituted or C$_1$–C$_4$-alkyl-, C$_1$–C$_4$-alkoxy-, C$_1$–C$_4$-haloalkyl-, C$_1$–C$_4$-haloalkoxy- or halogen-substituted 5- or 6-membered saturated or unsaturated heterocycle selected from the group consisting of tetrahydrofuranyl, tetrahydrothienyl, pyrrolidinyl, isoxazolidinyl, isothiazolidinyl, pyrazolidinyl, oxazolidinyl, thiazolidinyl, imidazolidinyl, 1,2,4-oxadiazolidinyl, 1,2,4-thiadiazolidinyl, 1,2,4-triazolidinyl, 1,3,4-oxadiazolidinyl, 1,3,4-thiadiazolidinyl, 1,3,4-triazolidinyl, 2,3-dihydrofuranyl, 2,5-dihydrofuranyl, 2,3-dihydrothienyl, 2,5-dihydrothienyl, 2,3-dihydropyrrolyl, 2,5-dihydropyrrolyl, 2,3-dihydroisoxazolyl, 4,5-dihydroisoxazolyl, 2,5-dihydroisoxazolyl, 2,5-dihydroxazolyl, 2,3-dihydroisothiazolyl, 4,5-dihydroisothiazolyl, 2,5-dihydroisothiazolyl, 2,3-dihydropyrazolyl, 4,5-dihydropyrazolyl, 2,5-dihydropyrazolyl, 2,3-dihydrooxazolyl, 4,5-dihydrooxazolyl, 2,5-dihydrooxazolyl, 2,3-dihydrothiazolyl, 4,5-dihydrothiazolyl, 2,5-dihydrothiazolyl, 2,3-dihydroimidazolyl, 4,5-dihydroimidazolyl, 2,5-dihydroimidazolyl, morpholinyl, piperidinyl, tetrahydropyridazinyl, tetrahydropyrimidinyl, tetrahydropyrazinyl, 1,3,5-tetrahydrotriazinyl, 1,2,4-tetrahydrotriazinyl, 1,3-dihydrooxazinyl, 1,3-dithianyl, tetrahydropyranyl, tetrahydrothiopyranyl, 1,3-dioxolanyl, 1,1-dioxo-2,3,4,5-tetrahydrothienyl, 1,3-dihydrooxazinyl, furyl, thienyl, pyrrolyl, isoxazolyl, isothiazolyl, pyrazolyl, oxazolyl, thiazolyl, imidazolyl, 1,2,4-oxadiazolyl, 1,2,4-thiadiazolyl, 1,2, 4triazolyl, tetrazolyl, 1,3,4-oxadiazolyl, 1,3,4-thiadiazolyl, 1,3,4-triazolyl, pyridyl, pyridazinyl, pyrimidinyl, pyrazinyl, 1,3,5-triazinyl, 1,2,4-triazinyl, 1,2,4,5-tetrazinyl;

$R^4$ is $C_1$–$C_4$-alkyl or $C_1$–$C_4$-haloalkyl;
$R^7$ is hydrogen, $C_1$–$C_4$-alkyl or $C_1$–$C_4$-haloalkyl;
n is 0, 1, 2;
X is chlorine or bromine.

2. A process for preparing the benzoylpyrazole, of formula II defined in claim 1, which comprises reacting a benzoylpyrazolone of formula V,

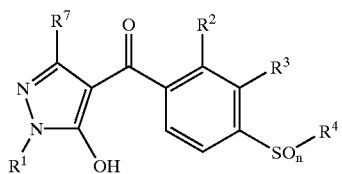

with an acyl halide.

3. The benzoylpyrazole defined in claim 1, wherein X is chlorine.

4. The benzoylpyrazole defined in claim 1, wherein $R^7$ is hydrogen.

5. The benzoylpyrazole defined in claim 1, wherein $R^1$ is $C_1$–$C_4$-alkyl.

6. The benzoylpyrazole defined in claim 1, wherein $R^2$ is $C_1$–$C_4$-alkyl.

7. The benzoylpyrazole defined in claim 1, wherein $R^2$ is methyl.

8. The benzoylpyrazole defined in claim 1, wherein $R^2$ is halogen.

9. The benzoylpyrazole defined in claim 1, wherein $R^2$ is chlorine.

10. The benzoylpyrazole defined in claim 1, wherein $R^3$ is unsubstituted or fluorine-, chlorine- methyl- or methoxy-substituted 2-furyl, 3-furyl, 2-thienyl, 3-thienyl, 4,5-dihydroisoxazol-3-yl, isoxazol-5-yl, isoxazol-3-yl, pyrazol-1-yl, pyrazol-5-yl, oxa-zol-2-yl, 4,5-dihydrooxazol-2-yl, 1,3-dioxolan-2-yl, 1,3-dithiolan-2-yl, thiazol-2-yl, thiazol-5-yl, thiazol-4-yl, 1,2,4-triazol-1-yl, 1,3,4-oxadiazol-2-yl, 2-pyridyl, 3-pyridyl, 4-pyridyl, pyrimidin-2-yl, pyrimidin-4-yl, 1,3-dioxan-2-yl or 1,3-dithian-2-yl.

11. The benzoylpyrazole defined in claim 1, wherein $R^3$ is unsubstituted or fluorine-, chlorine-, methyl- or methoxy-substituted 2-furyl, 3-furyl, 2-thienyl, 3-thienyl, 4,5-dihydroisoxazol-3-yl, isoxazol-5-yl, isoxazol-3-yl, pyrazol-1-yl, pyrazol-5-yl, oxazol-2-yl, 4,5-dihydrooxazol-2-yl, 1,3-dioxolan-2-yl, 1,3-dithiolan-2-yl, thiazol-2-yl, thiazol-5-yl, thiazol-4-yl, 1,2,4-triazol-1-yl, 1,3,4-oxadiazol-2-yl, 2-pyridyl, 3-pyridyl, 4-pyridyl, pyrimidin-2-yl, pyrimidin-4-yl, 1,3-dioxan-2-yl or 1,3-dithian-2-yl.

12. The benzoylpyrazole defined in claim 1, wherein $R^3$ is unsubstituted of fluorine-, chlorine-, methyl- or methoxy-substituted 4,5-dihydroisoxazol-3-yl, isoxazol-5-yl or isoxazol-3-yl.

13. The benzoylpyrazole defined in claim 1, wherein n is two.

14. The benzoylpyrazole defined in claim 1, wherein $R^4$ is $C_1$–$C_4$-alkyl.

15. The benzoylpyrazole defined in claim 1, wherein $R^2$ and $R^4$ are $C_1$–$C_4$-alkyl groups, $R^3$ is an unsubstituted or fluorine-, chlorine-, methyl- or methoxy-substituted 4,5-dihydroisoxazol-3-yl, isoxazol-5-yl or isoxazol-3-yl group, n denotes two, and X is chlorine.

* * * * *